(12) United States Patent
Garcia-Bengochea et al.

(10) Patent No.: US 11,944,353 B2
(45) Date of Patent: Apr. 2, 2024

(54) IMPLANTS AND INSTRUMENTS FOR ENHANCING VERTEBRAL ALIGNMENT AND SAGITTAL BALANCE

(71) Applicant: JGMG BENGOCHEA, LLC, Jacksonville, FL (US)

(72) Inventors: Javier Garcia-Bengochea, Jacksonville, FL (US); Marc von Amsberg, Waxhaw, NC (US)

(73) Assignee: JGMG BENGOCHEA, LLC, Jacksonville, FL (US)

(*) Notice: Subject to any disclaimer, the term of this patent is extended or adjusted under 35 U.S.C. 154(b) by 418 days.

(21) Appl. No.: 17/153,559

(22) Filed: Jan. 20, 2021

(65) Prior Publication Data

US 2021/0161567 A1    Jun. 3, 2021

Related U.S. Application Data

(62) Division of application No. 15/818,005, filed on Nov. 20, 2017, now Pat. No. 10,898,240.

(60) Provisional application No. 62/461,706, filed on Feb. 21, 2017, provisional application No. 62/424,228, filed on Nov. 18, 2016.

(51) Int. Cl.
   *A61B 17/70*    (2006.01)
   *A61B 17/00*    (2006.01)

(52) U.S. Cl.
   CPC ...... *A61B 17/7032* (2013.01); *A61B 17/7002* (2013.01); *A61B 17/7005* (2013.01); *A61B 17/7035* (2013.01); *A61B 17/7079* (2013.01); *A61B 17/708* (2013.01); *A61B 17/7086* (2013.01); *A61B 17/7089* (2013.01); *A61B 17/7091* (2013.01); *A61B 2017/0046* (2013.01); *A61B 17/7074* (2013.01)

(58) Field of Classification Search
   CPC .................................. A61B 17/7035–17/7038
   See application file for complete search history.

(56) References Cited

U.S. PATENT DOCUMENTS

| | | |
|---|---|---|
| 5,540,688 A | 7/1996 | Navas |
| 5,776,135 A | 7/1998 | Errico et al. |
| 6,585,738 B1 | 7/2003 | Mangione et al. |
| 6,660,005 B2 | 12/2003 | Toyama et al. |
| 6,802,844 B2 | 10/2004 | Ferree |
| 7,207,992 B2 | 4/2007 | Ritland |
| 7,662,172 B2 | 2/2010 | Warnick |
| 7,708,762 B2 | 5/2010 | McCarthy et al. |
| 7,749,258 B2 | 7/2010 | Biedermann et al. |

(Continued)

FOREIGN PATENT DOCUMENTS

| | | |
|---|---|---|
| DE | 202011100080 | 4/2011 |
| EP | 2737866 A1 | 8/2009 |

(Continued)

*Primary Examiner* — Julianna N Harvey
(74) *Attorney, Agent, or Firm* — McNees Wallace & Nurick LLC

(57) ABSTRACT

Spinal stabilization implant assemblies, as well as systems, instruments and methods are provided for implanting and stabilizing adjacent vertebra in connection with a surgical procedure, particularly a spinal surgery. The implant assemblies and instruments enable controlled spinal rod insertion and reduction, and controlled rotation or de-rotation of adjacent spinal bones for optimized compression to achieve enhanced sagittal balance in a treated spine.

11 Claims, 9 Drawing Sheets

(56) References Cited

U.S. PATENT DOCUMENTS

| | | |
|---|---|---|
| 7,753,939 B2 | 7/2010 | Ritland |
| 7,758,584 B2 | 7/2010 | Bankoski et al. |
| 7,828,824 B2 | 11/2010 | Kwak et al. |
| 7,833,251 B1 | 11/2010 | Ahlgren et al. |
| 7,854,752 B2 | 12/2010 | Colleran et al. |
| 7,862,587 B2 | 1/2011 | Jackson |
| 8,012,186 B2 | 9/2011 | Pham et al. |
| 8,038,701 B2 | 10/2011 | Rock et al. |
| 8,167,912 B2 | 5/2012 | Jacofsky et al. |
| 8,277,490 B2 | 10/2012 | Freeman et al. |
| 8,298,268 B2 | 10/2012 | Marino et al. |
| 8,298,275 B2 | 10/2012 | Rezach |
| 8,382,805 B2 | 2/2013 | Wang et al. |
| 8,430,914 B2 | 4/2013 | Spratt et al. |
| 8,647,370 B2 | 2/2014 | Barry |
| 8,784,424 B2 * | 7/2014 | Tsuang ............... A61B 17/1757 606/86 A |
| 8,801,757 B2 | 8/2014 | Abdou |
| 8,808,379 B2 | 8/2014 | Abdou |
| 8,852,239 B2 | 10/2014 | Jackson et al. |
| 8,956,361 B2 | 2/2015 | Davenport et al. |
| 8,986,349 B1 | 3/2015 | German et al. |
| 9,138,261 B2 | 9/2015 | Di Lauro et al. |
| 9,216,039 B2 | 12/2015 | Jackson |
| 9,295,494 B2 | 3/2016 | Strauss et al. |
| 9,345,519 B1 | 5/2016 | Poirier et al. |
| 9,517,089 B1 | 12/2016 | Casey et al. |
| 9,603,632 B1 | 3/2017 | Gunn et al. |
| 9,737,339 B2 | 8/2017 | Copp et al. |
| 2007/0270842 A1* | 11/2007 | Bankoski ............. A61B 17/865 606/86 A |
| 2008/0183223 A1 | 7/2008 | Jeon et al. |
| 2009/0062914 A1 | 3/2009 | Marino |
| 2010/0100137 A1* | 4/2010 | Justis ................. A61B 17/7037 606/301 |
| 2011/0077692 A1* | 3/2011 | Jackson ............. A61B 17/7089 606/305 |
| 2012/0253400 A1 | 10/2012 | Clark et al. |
| 2012/0296380 A1 | 11/2012 | Simonson |
| 2013/0325069 A1 | 12/2013 | Pereiro de Lamo et al. |
| 2014/0012321 A1* | 1/2014 | Hutton ............... A61B 17/7086 606/279 |
| 2015/0025578 A1 | 1/2015 | James et al. |
| 2015/0127054 A1 | 5/2015 | Tsuang et al. |
| 2015/0265315 A1 | 9/2015 | Sims et al. |
| 2016/0361095 A1 | 12/2016 | Burdi et al. |
| 2017/0020573 A1 | 1/2017 | Cain et al. |
| 2017/0035462 A1 | 2/2017 | George et al. |
| 2017/0311988 A1 | 11/2017 | Petit |

FOREIGN PATENT DOCUMENTS

| | | |
|---|---|---|
| WO | 2006127992 A2 | 11/2006 |
| WO | 2015164051 A1 | 10/2015 |

* cited by examiner

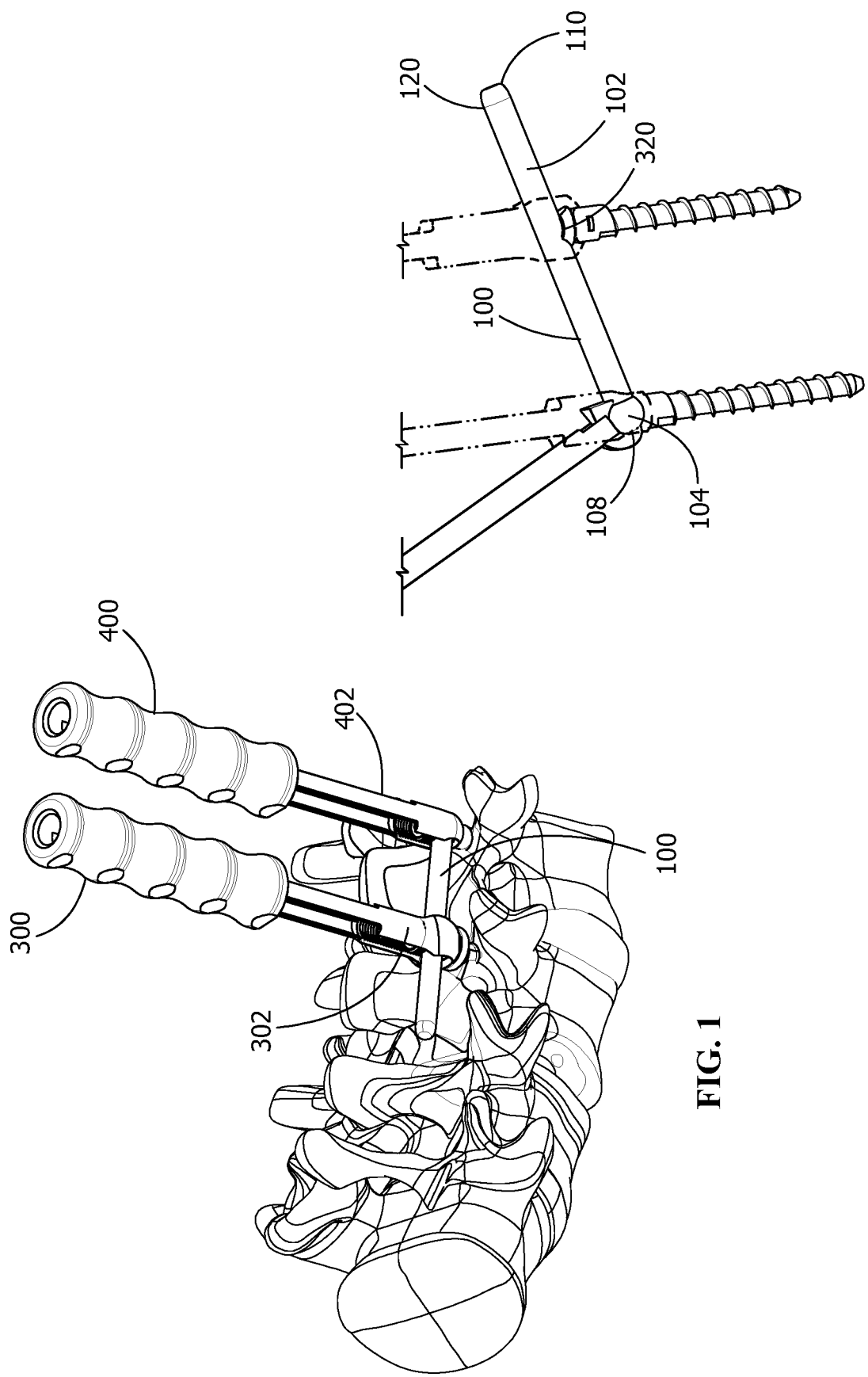

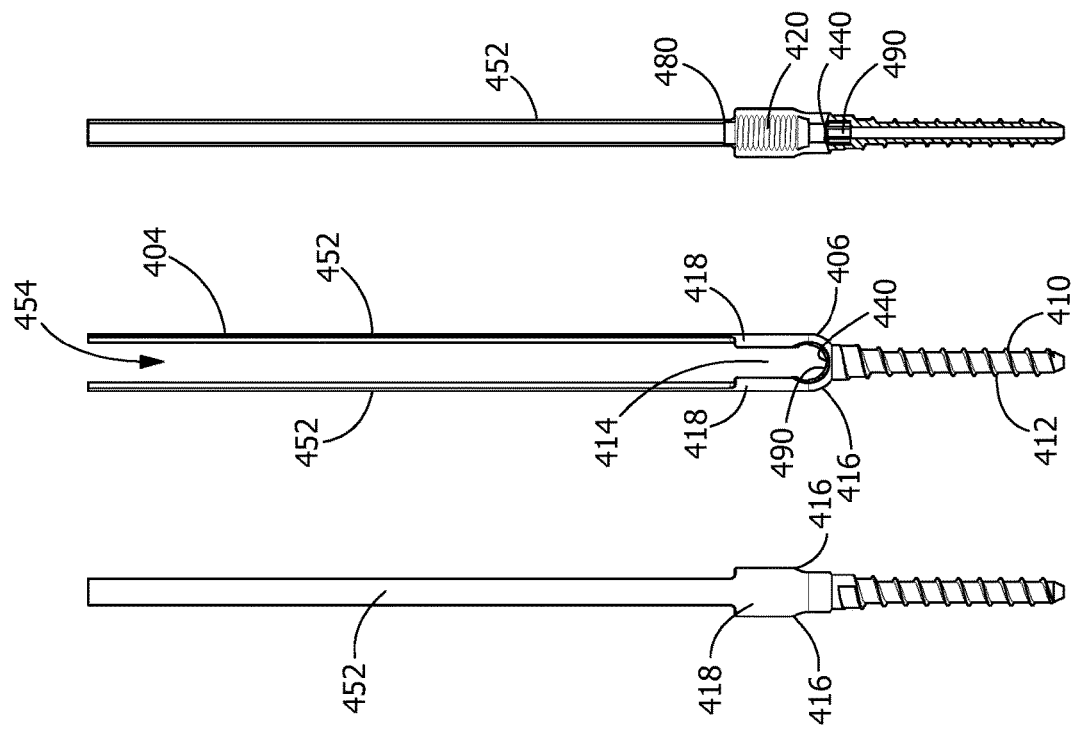
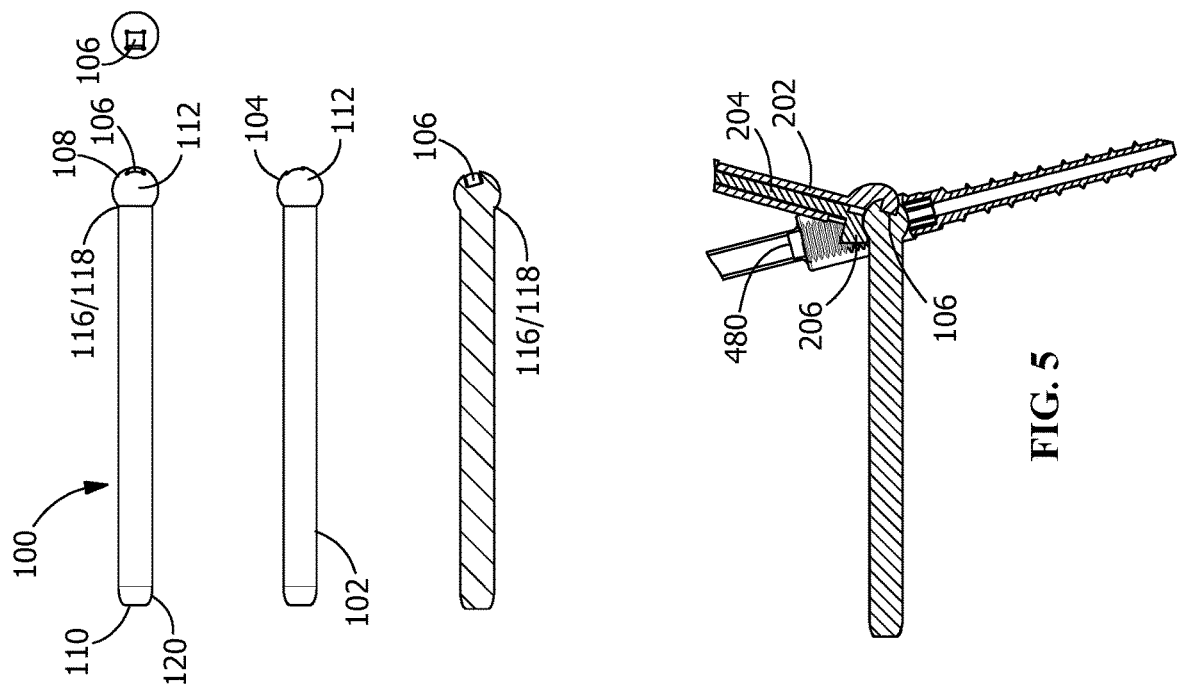
FIG. 6
FIG. 5

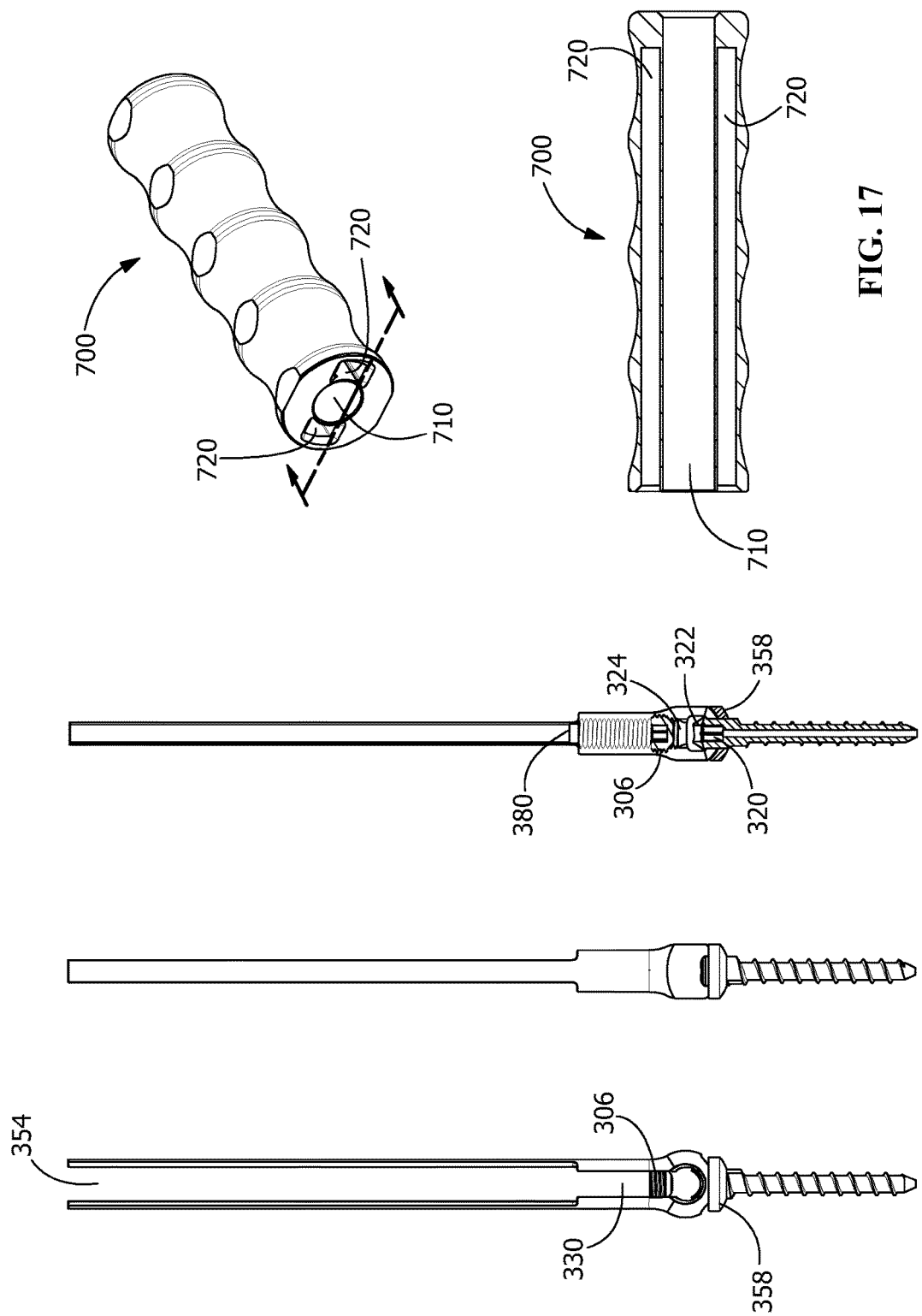

IMPLANTS AND INSTRUMENTS FOR ENHANCING VERTEBRAL ALIGNMENT AND SAGITTAL BALANCE

This application is a divisional application of U.S. Nonprovisional patent application Ser. No. 15/818,005, filed Nov. 20, 2017, entitled "Implants and Instruments for Enhancing Vertebral Alignment and Sagittal Balance" which has issued as a U.S. patent Ser. No. 10898240, issued on Jan. 26, 2021, and which claims the benefit of U.S. Provisional Patent Application Ser. No. 62/424,228, filed on Nov. 18, 2016, entitled "Implants and Instruments for Enhancing Vertebral Alignment and Sagittal Balance", and U.S. Provisional Patent Application Ser. No. 62/461,706, filed on Feb. 21, 2017, entitled "Implants and Instruments for Enhancing Vertebral Alignment and Sagittal Balance, Pivoting Screws," each of which is incorporated herein by reference in its entirety.

FIELD OF THE INVENTION

The present invention is directed to spinal stabilization rods, screws, assemblies, and systems, together with instruments and methods for adjusting a spine. More particularly, the present invention is directed to spinal stabilization rods, spinal stabilization screws, spinal stabilization assemblies, and spinal stabilization systems for achieving sagittal balance in connection with spinal surgeries, and methods for adjusting a spine with surgical intervention.

BACKGROUND OF THE INVENTION

A human spine includes three main regions, which in the direction from head to toe, includes cervical, thoracic, and lumbar regions. A normal spine is characterized by as having a generally soft "S" shape, where the cervical region has a slightly forward (lordotic) curvature from the base of the skull toward the thoracic region, and a soft backward (kyphotic) curvature in the thoracic region, and a soft forward (lordotic) curvature in the lumbar region toward the sacrum. In those individuals who suffer from spinal defects stemming from congenital, degenerative disease, and other pathology or injury, the normal curvature of the spine can be compromised. Such defects often can manifest as deviations from this typical S curvature, and may be generally characterized as sagittal imbalance. Other deformities and defects can cause the spine to deviate laterally along its longitudinal axis, such deformities including scoliosis.

Sagittal imbalance refers to any of a variety of conditions where the normal alignment of the spine is disrupted in the sagittal plane (the plane that divides the body front to back) characterized by a deformation of the spinal curvature from the soft S shape. Examples of sagittal imbalance include kyphotic curvature in the lumbar spine (curving backward rather than forward, giving the spine an overall C shape), lumbar hyperlordosis (excessive forward curvature in the lumbar spine), a lack of curvature in the lumbar spine often referred to as flat back syndrome, thoracic hyperkyphosis (excessive backward curvature in the thoracic spine causing hunching), and cervical hyperlordosis (excessive forward curvature in the cervical spine). In addition to the problems related to any underlying or causative pathology, these imbalances also have significant adverse effects on the patient, contributing to an overall hindrance of mobility and normal biomechanics, as well as pain.

Treatments that address underlying pathology and aim to address sagittal imbalance defects generally involve surgical procedures. Similarly, treatments of scoliotic defects can be addressed with surgical procedures. Some treatments involve displacement or removal of portions of vertebral bone, and in some cases entire vertebra. Some procedures involve removal of spinal disc material and replacement with implants that aim to restore the native spinal curvature and spacing, and either restore motion between the adjacent vertebrae, or fuse the vertebrae together. The various surgical procedures may be performed by fully open surgical approaches and by a variety of minimally invasive approaches (e.g., percutaneous access to the spine). In each of the various procedures, spinal screws, in some examples, screws intended for implantation in a pedicle, are typically implanted in spinal bones, such as, for example, in the including for example in the sacrum, or in the pedicles or other portions of one or more vertebrae, or for example in one or more portions of at least two adjacent vertebrae, to provide stabilization and/or correction. Other applications of spinal screws involve implantation of screws into other portions of spinal bones, and the screws are used in different numbers and combinations.

Direct open access offers the greatest opportunity for the surgeon to manipulate the tissue to achieve the desired spinal correction using implants and instruments. But open access also has a variety of problems related to the level of invasiveness resulting in significant soft tissue damage, blood loss, significant time under anesthesia, and associated painful and protracted recovery time. In contrast, minimally invasive approaches are far less invasive, can be completed faster, and can result in much less damage to soft tissue allowing faster recovery and less pain and discomfort. Yet, minimally invasive procedures can be more complicated due to the limited ability of the surgeon to adequately visualize the target tissue and the limited space within which to maneuver instruments and implants. In particular, percutaneous access can present challenges in achieving the alignment of sequentially placed instruments and implants along the spine, and in achieving fixation of the target vertebrae to provide the enhanced improvement to sagittal imbalances.

Accordingly, what is need in the art are instruments and implants that can be manipulated via an open or a percutaneous access route to allow for enhanced positioning and alignment of stabilizing implants to achieve fixation that meaningfully improves restoration of normal spinal curvature and sagittal balance.

BRIEF DESCRIPTION OF THE INVENTION

In one exemplary embodiment, a method for adjusting a spine that is defined by a sagittal plane, a frontal plane and a transverse plane includes providing one or more fixation screws that are adapted for implantation in the spine. In some particular embodiments, the fixation screws are spinal screws, and in some embodiments, are screws for implantation into the pedicle of a vertebra, each fixation screw having a generally U-shaped aperture for receiving a spinal stabilization rod. According to the various embodiments, at least one of the fixation screws is adapted to one or more of a pivot in the transverse plane and rotate on an axis in the transverse plane to enable additional degrees of freedom for aligning and engaging the stabilization rod within the generally U-shaped apertures of the fixation screws. According to the method, the fixation screws, when implanted in adjacent vertebrae and when interconnected by passage of the rod through their generally U-shaped apertures along an axis in the sagittal plane, are rigid in the sagittal plane to enable their use as a fulcrum for rotation of the vertebrae in the sagittal plane. According to some embodiments, at least one of the fixation screws is adapted to pivot in the transverse plane within a range from about 5 degrees to about 25 degrees. According to some embodiments, at least one of the fixation screws is adapted to rotate on an axis in the transverse plane within a range from about 5 degrees to about 10 degrees.

In another exemplary embodiment, a method for adjusting a spine includes providing a surgical stabilization system including a plurality of fixation screw assemblies, at least one such assembly selected from embodiments of the monoaxial screw assembly and the pivoting screw assembly disclosed herein, the remaining assemblies selected from conventional fixation screws, in some particular embodiments, spinal screws selected from pedicle screw assemblies and embodiments of the monoaxial screw assembly and pivoting screw assembly disclosed herein. The method further includes implanting in a first vertebra the at least one pedicle screw assembly selected from embodiments of the monoaxial screw assembly and pivoting screw assembly disclosed herein and implanting another pedicle screw assembly in a vertebra that is adjacent to the first vertebra between which vertebrae is an intervertebral disc space. The spinal assemblies may be implanted in any order. The method further includes positioning the head of a stabilization rod having at least one curved surface into contact with a seat of at least one fixation screw assembly selected from embodiments of the monoaxial screw assembly and pivoting screw assembly disclosed herein, and provisionally locking the head into the seat, rotating the vertebra in the sagittal plane (in a direction that is either cranial or caudal) so as to either compress or distract the intervertebral space, and locking the spinal stabilization rod into each of the assemblies to fix the position of the vertebrae.

In another exemplary embodiment, a spinal stabilization fixation screw assembly according to the disclosure includes a fixation screw assembly, and a compression component engageable within a receiver body of the fixation screw assembly to secure a stabilization rod therein. The assembly thus includes a spinal stabilization rod for surgical implantation that includes a first terminus and a second terminus, a head and a shaft disposed between the first terminus and the second terminus, the head including a curved contact surface, and an engagement recess disposed in the curved contact surface.

In another embodiment, a spinal stabilization fixation screw assembly according to the disclosure includes a monoaxial fixation screw assembly that includes a monoaxial fixation screw having a shank that extends from a receiver body, the receiver body and shank being fixedly engageable with one another along a shared central axis, the shank having threads to engage bone and the receiver body having opposing sidewalls, forming a generally U-shaped aperture, threads on at least a portion of an interior side of the sidewalls, and a seat for receiving the stabilization rod head, the seat including at least one spherical surface. The stabilization fixation screw assembly also includes a pair of elongate opposing slats extending from the receiver body defining a central passage having a first end that opens into the central passage, and a second end releasably engageable with the receiver body of the monoaxial fixation screw. The stabilization fixation screw assembly also includes a generally cylindrical compression component configured to engage a portion of the central bore of the receiver body and be complimentarily received therein, the compression component configured to compress the head of the stabilization rod into the seat of the receiver body to lock the position of the stabilization rod relative to the monoaxial fixation screw, and having a contact surface for compressible engagement with the stabilization rod head and a peripheral edge having on at least a portion of its surface threads that are engageable within the seat of the receiver body of the monoaxial fixation screw. According to the embodiment, the stabilization rod is sized for insertion through the central passage and through the generally U-shaped aperture for engagement of the stabilization rod head within the receiver body seat.

In another exemplary embodiment, a pivoting screw assembly for surgical implantation includes a fixation screw that includes a threaded shank, and a head that has a proximal portion and a distal portion. The proximal portion includes a concave curved cradle that is shaped and disposed to receive and support a cylindrical stabilization rod, and a tapered surface that is distal to the curved cradle of the screw head and adjacent to the threaded shank, the tapered surface including a linear taper, a curved taper, or a combination thereof.

The pivoting screw assembly also includes a receiver body adapted for engagement with the fixation screw and having a generally U-shaped conformation, and including a base that includes a curved exterior surface, an interior surface having a through slot for receiving the shank and a seat with a curved surface for contacting the tapered surface of the fixation screw. The receiver body also includes opposing sidewalls extending from the base, the opposing sidewalls including interior and exterior surfaces, and including on the interior surfaces opposing flats adjacent to the base and a threaded portion proximal to the flats. The base and the opposing sidewalls are shaped and disposed to receive the spinal stabilization rod in contact with the cradle of the screw head inserted in the through slot. The curved exterior surface of the base and the curved surface of the seat of the base include an essentially common curvature.

The pivoting screw assembly also includes a generally cylindrical compression component including a threaded surface disposed and arranged to engage with the threaded portions on the interior surfaces of the opposing sidewalls of the receiver body, the compression component shaped to contact and compress the head or a shaft of a spinal stabilization rod in contact with the cradle of the screw head.

The pivoting screw assembly also includes on the receiver body a pair of elongate portion which in some embodiments include opposing slats, extending from above the threaded portion away from the seat and defining a central passage. In those embodiments that comprise a pair of elongate opposing slats, the opposing slats are removably attached to the receiver body. In some such embodiments, the slats are unitary with the receiver body and include a score for removal.

In another exemplary embodiment, a pivoting screw assembly for surgical implantation includes a fixation screw, a receiver body adapted for engagement with the fixation screw, and a generally cylindrical compression component. The fixation screw includes a shank, a screw head, and a tapered surface. The shank includes a thread arranged and shaped to engage bone. The screw head includes a proximal surface, a distal surface, a drive recess, and a cradle. The cradle is disposed at the proximal surface and extends from the screw head and away from the shank. The cradle includes at least two opposing arms defining a curved cradle surface shaped and disposed to receive and support a spinal stabilization rod. The tapered surface joins the distal surface of the screw head and the shank, and includes a linear taper, a curved taper, or a combination thereof. The receiver body is adapted for engagement with the fixation screw, and includes an aperture having a generally U-shaped conformation, a base, and opposing sidewalls extending from the base. The base includes a curved exterior surface, an interior surface having a through slot for receiving the shank, and a seat with a curved surface for contacting the tapered surface of the fixation screw. The opposing sidewalls include opposing flats on a sidewall interior surface adjacent to the base, and a threaded portion proximal to the opposing flats. The base and the opposing sidewalls are shaped and disposed to receive and support the spinal stabilization rod in contact with the cradle of the screw head. The generally cylindrical compression component includes a threaded surface disposed and arranged to engage with the threaded portion of the opposing sidewalls of the receiver body and compress against the spinal stabilization rod, compressing the spinal stabilization rod into the cradle of the screw head. The curved exterior surface of the base and the curved surface of the seat of the base include an essentially common curvature.

In another exemplary embodiment, a spinal stabilization system for surgical implantation, includes an inserter tool. The inserter tool includes an elongate body, a handle at a first end of the elongate body, an actuating knob, and an engagement projection at the second end of the elongate body. The engagement projection is shaped and disposed to mate with an engagement recess of the spinal stabilization rod, and the inserter tool is adjustable from the handle to disengage from the engagement recess. In one embodiment, the engagement recess is disposed to mate with a retention projection of an inserter tool, and the rod head includes a further recess disposed to contact a locking projection of the inserter tool by insertion of an engagement feature on the tool into the further recess. In another embodiment, the engagement recess is disposed to mate with a retention projection of an inserter tool, and the rod head includes a surface disposed to contact a locking projection of the inserter tool without insertion of an engagement feature on the tool.

Other features and advantages of the present invention will be apparent from the following more detailed description of the preferred embodiment, taken in conjunction with the accompanying drawings, which illustrate, by way of example, the principles of the invention.

BRIEF DESCRIPTION OF THE DRAWINGS

FIG. 1 fixation screw assemblies, more particularly embodiments of each of a monoaxial screw assembly and a pivoting screw assembly in the context of spinal anatomy;

FIG. 2 shows components of the assembly of FIG. 1, absent the spinal anatomy;

FIG. 5 shows, in alternate views, a representative embodiment of a spherical headed rod implant according to the disclosure, and in cross-sectional view, representative embodiments of a spherical headed rod in the context of the fixation screw seat in accordance with the disclosure, the inserter and rod depicted in an engaged configuration;

FIG. 6 shows, in alternate views, a representative embodiment of a fixation screw having an aperture having a generally U-shaped conformation according to the disclosure;

FIG. 16 shows alternate side views and a side cross-sectional view of the pivoting screw assembly of FIG. 14;

FIG. 17 shows a bottom perspective view of a grip handle for affixing to the opposing elongate slats of one of the inventive assemblies hereof, including openings for receiving the slats, and a through channel for receiving insertion of one or more of screws, set screws, rods and drivers; and, FIG. 18 shows alternative bottom perspective views and a side cross-sectional view of the seat component of the pivoting screw assembly shown in FIG. 14.

Throughout the disclosure and the drawings, the same reference numbers will be used to represent the same parts.

Figure 3A:
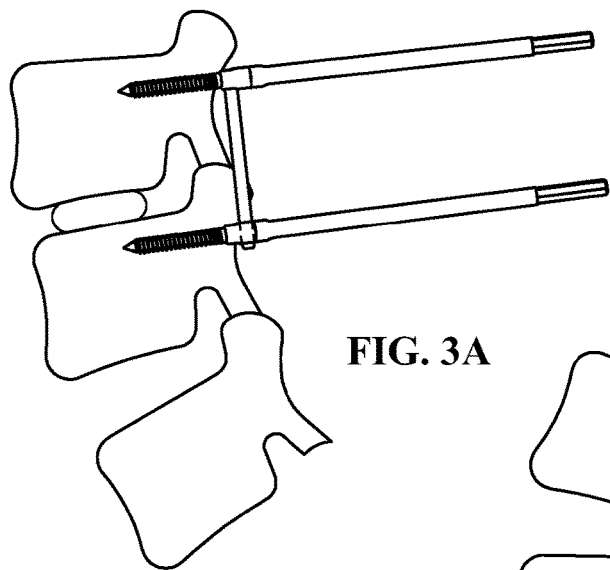
FIG. 3A shows a technique of implant placement and engagement as part of a schematic that shows successive configurations of representative embodiments of certain implants and instruments according to the disclosure in the context of a spinal construct.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

Provided are exemplary embodiments of the present disclosure, in comparison to articles and methods not utilizing one or more features disclosed herein, enhance positioning and alignment of stabilizing implants to achieve fixation that restores normal spinal curvature and sagittal balance, minimize invasiveness of surgical intervention, increase precision and control of spinal rod insertion and reduction, optimize spinal compression, or combinations thereof.

In accordance with the disclosure, implants, instruments, and surgical techniques are provided for stabilizing adjacent vertebra and achieving enhanced sagittal balance in connection with a surgical procedure, particularly a spinal surgery. The implants and instruments enable precise and controlled spinal rod insertion and reduction, and controlled rotation or de-rotation of adjacent vertebrae in the sagittal plane for optimized compression to achieve enhanced sagittal balance in the spine of the clinical subject.

The implants and instruments according to the disclosure are useful for any mode of spinal access, and in particular in the context of a percutaneous (minimally invasive) procedure, whereby an inventive implant assembly serves as a fulcrum to permit rotational movement of one vertebral body relative to an adjacent vertebral body/ies in the sagittal plane (cranial to caudal axis). The inventive assemblies allow for a significant enhancement in the effective rotation and compression relative to the adjacent vertebra as compared to what is achieved with other assemblies known in the art. In particular, the implant systems provide fixation screws that are essentially rigid in the sagittal plane to enable their use as a fulcrum for rotation of the vertebrae in the sagittal plane, and include screws that can rotate in the transvers plane to enable additional degrees of freedom as compared to devices in the art, thus optimizing alignment and engagement of a stabilization rod along the longitudinal axis of the spine.

As described herein, the exemplified fixation screw embodiments are from time to time described in the context of use for spinal surgery, and in particular for surgery involving the implantation of the fixation screws into the pedicles of adjacent vertebrae of the spine. It will be appreciated that fixation screws, particularly spinal fixation screws, may be implanted in other structures of spinal bones, and may be used in combinations and arrangements that vary from those described herein. Thus, it is expressly intended that the inventive assemblies, systems and methods hereof are more generally applied to applications that are not limited to implantation and manipulation of the spine by implantation in pedicles. While reference may be made in the examples and descriptions herein to applications involving fixation within pedicles, these examples and described embodiments are not limiting.

Generically, fixation screw assemblies include a fixation screw, typically having a threaded shank arranged and shaped to engage bone, and a head, a receiver body (typically referred to in the art as a tulip head), a generally cylindrical rod that is placed along the longitudinal axis of the spine between two fixation screws, and a generally cylindrical compression component (e.g., a set screw). Other components may also be present. The receiver body generically includes an aperture having a generally U-shaped conformation for supporting the rod, a base, and opposing sidewalls having a threaded portion for engaging with the compression component.

Three main types of fixation screw assemblies are well known in the art. A monoaxial screw assembly means and refers to an assembly in which the receiver body is free to rotate about and may be free to translate vertically along the axis of the screw, or is rigidly fixed to the screw, and cannot translate in a plane that is transverse to the screw axis. A uniaxial screw means and refers to an assembly in which the receiver body is free to rotate about and may be free to translate vertically along the axis of the screw, and is limited to translate in only one plane that is transverse to the screw axis. And a polyaxial screw means and refers to an assembly in which the receiver body is free to rotate about and may be free to translate vertically along the axis of the screw and is also free to swivel about the axis of the screw to provide a multi-directional variable angle between the shank of the screw and the receiver body such that the receiver body can translate in two or more planes that are transverse to the screw axis.

Polyaxial screws are the most commonly selected screw for degenerative spinal treatments to assist in coupling the screw with a longitudinal rod that is engaged with an adjacent screw assembly, even when the angles of the adjacent screws vary due to variations in the spinal anatomy. Polyaxial screws overcome the major limitation of monoaxial screws, which cannot be variably adjusted to accommodate variable rod trajectories, and thus can create the problem of high force loads at the screw-bone interface that can lead to screw failure. But polyaxial screws cannot be used to provide rotational control for vertebral body correction in the sagittal plane (along the length of the spine, cranial to caudal) or in the transverse plane (around the axis of the spine), thus limiting their usefulness for correcting scoliotic type deformities and for correcting sagittal balance. Uniaxial screws are designed to pivot in the sagittal plane along the axis of a rod placed through the generally U-shaped aperture, which provides some of the benefits of rod contact and capture in the sagittal plane, and the rigidity in the transverse plane allows for axial rotation of implanted vertebrae to address scoliotic deformity.

None of the conventional fixation screw and rod systems are designed to allow for both optimal rod trajectory and rotational adjustment of the vertebrae in the sagittal plane to correct lordotic and kyphotic imbalances.

Thus, in various embodiments, each of the inventive fixation screw assemblies herein provide for rod trajectory degrees of freedom that facilitate optimal rod trajectory for contacting and capturing the rod within adjacently implanted screw assemblies. In various embodiments, the fixation screw assemblies herein provide receiver body degrees of freedom that allow for rotational adjustability of implanted vertebrae in the sagittal plane to correct lordotic and kyphotic imbalances.

Surgical Implant Assemblies

The systems for spinal adjustment according to the disclosure, as described herein, include one or more of the inventive assemblies hereof, and may include one or more fixation screw assemblies that are generally known in the art.

As described herein above, conventional fixation screw assemblies and rod systems do not allow for both optimal rod trajectory and rotational adjustment of the vertebrae in the sagittal plane to correct lordotic and kyphotic imbalances. In various embodiments, each of the inventive fixation screw assemblies herein provide for one or more of the benefits of rod trajectory degrees of freedom and fixation screw receiver body degrees of freedom. Used alone or in combination with each other and with conventional fixation screw assemblies, the inventive assemblies hereof provide novel and unknown combined benefits that include both optimal rod trajectory and rotational adjustability of implanted vertebrae in the sagittal plane to correct lordotic and kyphotic imbalances.

Generally, there are two embodiments of inventive implant assemblies herein. Referring now to FIG. 1 and FIG. 2, the surgical implant assemblies according to the disclosure include a pivoting screw assembly 300 and monoaxial screw assembly 400 shown in the context of the spine in FIG. 1 and without the spine in FIG. 2, the two assemblies positioned for connection between them on adjacent vertebra.

It will be appreciated, as further described herein, that in some embodiments, only one of the inventive assemblies may be used for spinal fixation, and thus may be used with one or more other and conventional screw assemblies, while in other embodiments, a spinal fixation system may be comprised exclusively of one or combinations of the inventive implant assemblies. In some embodiments, the assemblies are employed in combinations wherein at least one monoaxial fixation screw assembly 400 is implanted in a first vertebra and at least one pivoting screw assembly 300 is implanted in a second and adjacent vertebra, as shown in FIG. 1, in some such embodiments wherein the monoaxial fixation screw assembly 400 is implanted caudally (toward the feet, or inferiorly) and the pivoting screw assembly 300 is implanted cranially (toward the head, or superiorly). In some embodiments, pairs of each of the respective assemblies are implanted in the two pedicles of the implanted vertebrae. Actuation of motion of the assemblies and rotation thereof to achieve spinal rotation in the sagittal plane is described herein below and in the claims. As described herein, the fixation screws may be implanted in a particular position relative to each other, such that in some embodiments, a fixation screw that is implanted in one vertebra and adjacent to another fixation screw in another vertebra may be implanted in either a caudal or a cranial orientation. Caudal oriented means in the vertebra closest to the feet and cranial oriented means in the vertebra closest to the head. While in some exemplary embodiment's an inventive fixation screw may be described as being implanted in a caudal orientation, such embodiments are not intended to be limiting; thus, each of the inventive fixation screw assemblies hereof, as well as any other fixation screws known in the art, may be implanted according to the methods hereof with a caudal or a cranial orientation relative to other fixation screws that may be used in a fixation system. Further, as described herein in some embodiments, the term adjacent refers to directly adjacent with respect to spinal bones, wherein there are no intervening bony structures or vertebrae between the referenced adjacent vertebrae. It will be appreciated that more generally in the various embodiments, adjacent may be directly adjacent or may be indirectly adjacent wherein there is one or more vertebrae between the described adjacent vertebrae. Thus, it is expressly intended that the inventive assemblies, systems and methods hereof may be employed generally to implantation arrangements that are not limiting with respect to cranial-caudal orientation or adjacency.

Figure 3B:
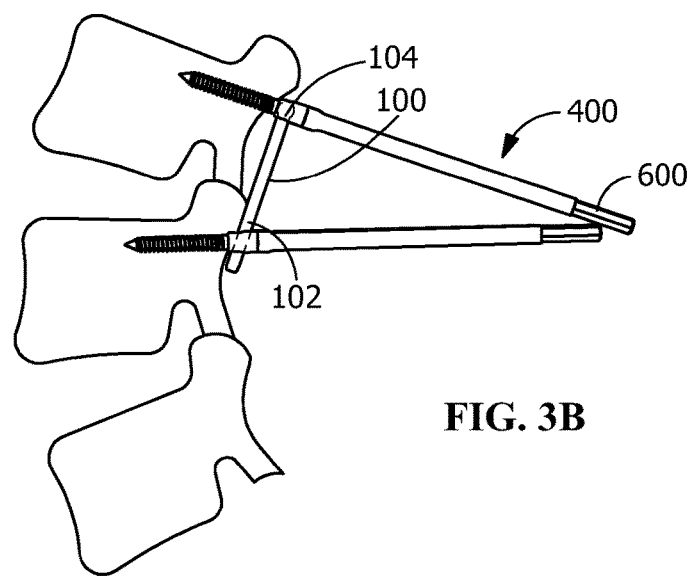
FIG. 3B shows a technique of manipulation by compression/rotation.
Figure 3C:
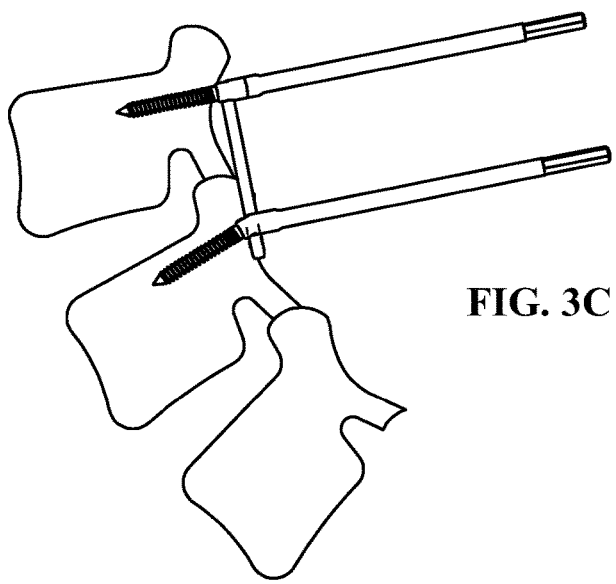
FIG. 3C shows a technique of implant fixation by locking.

Referring now to FIG. 3, a representative embodiment of an inventive surgical implant assembly comprising a monoaxial fixation screw assembly 400 according to the disclosure is depicted, together with a conventional surgical implant assembly. The assemblies as depicted are fixation screws for insertion into a pedicle of a vertebral body. In use, fixation screw assemblies implanted in pedicles are typically deployed in pairs, one fixation screw of each pair being secured to the respective left and right pedicles of a vertebra. In a representative embodiment, a system for stabilizing the spine includes two pairs of fixation screws on adjacent vertebra, wherein the system is used for a single level fusion surgery (placement of an interbody disc into a single disc space that is stabilized using the fixation screw assemblies interconnected by a pair of stabilization rods). As shown in FIG. 3, the inventive surgical assembly is affixed to the superior vertebra and a fixation screw is affixed to the adjacent inferior vertebra. Fixation and enhanced sagittal balance is achieved according to the methods as more fully described herein below.

Referring again to FIG. 1 and FIG. 2, it will be appreciated that within the systems hereof, the fixation screw configuration for the inventive monoaxial fixation screw assembly 400 as described herein is monoaxial, and the fixation screw configuration for the pivoting screw assembly 300 is as described herein, where the receiver body 304 has an inventive design for enabling unique pivotal movement relative to the fixation screw 302. Additional generic fixation screw assemblies used in the systems hereof may be one of mono-, uni- and polyaxial.

Spinal Stabilization Assemblies

Figure 4:
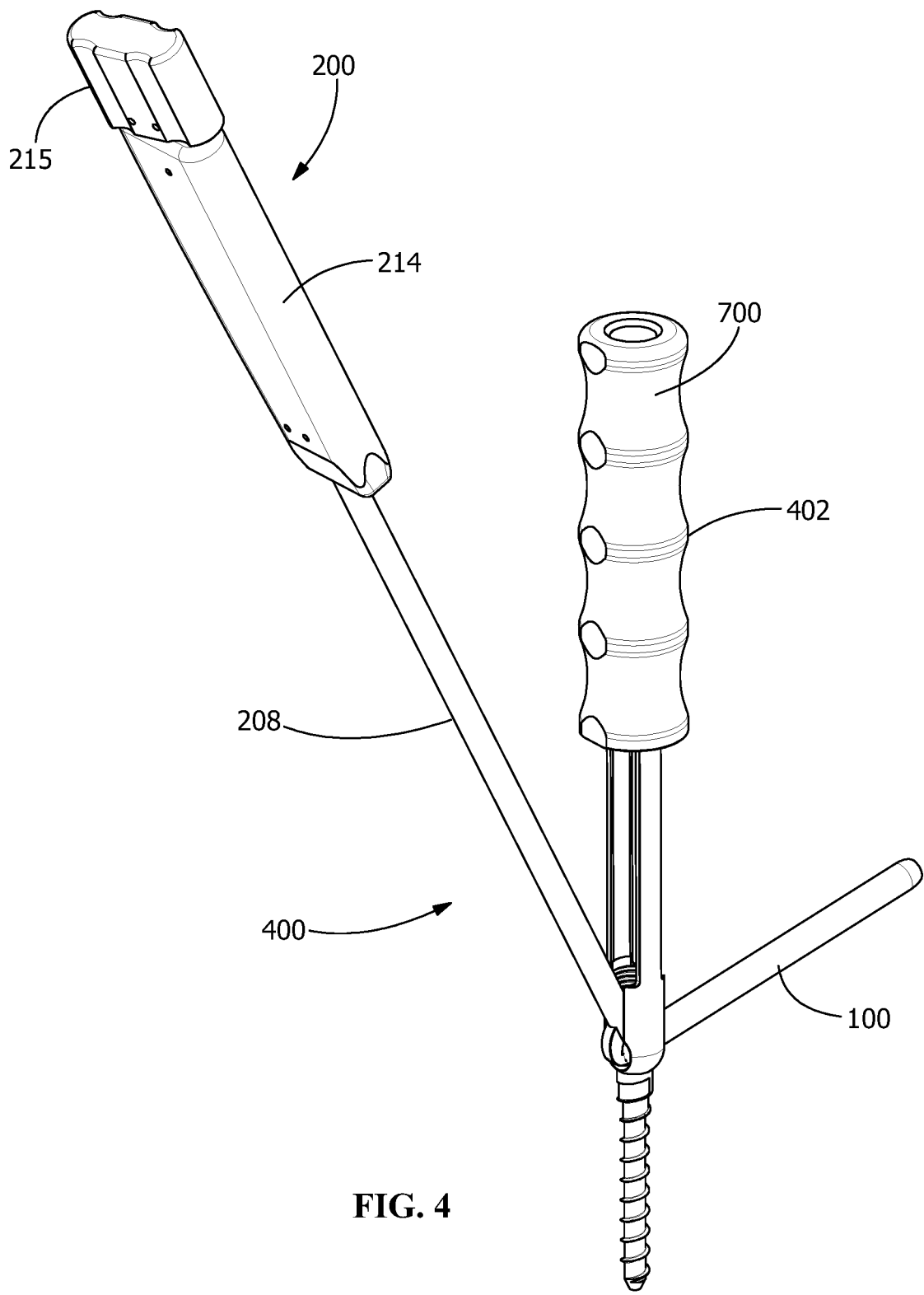
FIG. 4 shows a representative embodiment of the monoaxial screw assembly.

Referring now to FIG. 4, a representative embodiment of a spinal stabilization rod 100 useful with one or more of embodiments of fixation screws including a monoaxial fixation screw assembly 400 and a pivoting screw assembly 300. As depicted in FIG. 4, the assembly includes a spinal stabilization rod 100 that is affixed at a first terminus to an inserter tool 200, wherein the first terminus 108 is shown positioned within a monoaxial screw assembly 400. The various components of the assembly will now be described.

Referring now to FIG. 5, in one embodiment, a spinal stabilization rod 100 for surgical implantation includes a shaft 102, a head 104, and an engagement recess 106. The shaft 102 includes a first terminus 108 and a second terminus 110. The head 104 includes a curved contact surface 112, and the engagement recess 106 is disposed in the curved contact surface 112.

The head 104 may include any suitable conformation, including, but not limited to, a spheroidal conformation truncated at a juncture 118 between the head 104 and the shaft 102, a frusto-spheroidal conformation truncated at a juncture 118 between the head 104 and the shaft 102, or a combination thereof.

The second terminus 110 of the shaft 102 may include any suitable conformation, including, but not limited to a tapered conformation 120, a blunt conformation (not shown), and beveled conformation (not shown), a chamfered conformation (not shown), a semi-spheroidal conformation (not shown), a conical conformation (not shown), a frusto-conical conformation (not shown), or combinations thereof.

In one embodiment, the engagement recess 106 is disposed to mate with an engagement projection 202 of an inserter tool 200. In a further embodiment, the engagement recess 106 includes one or more recessed portions.

Figure 7:
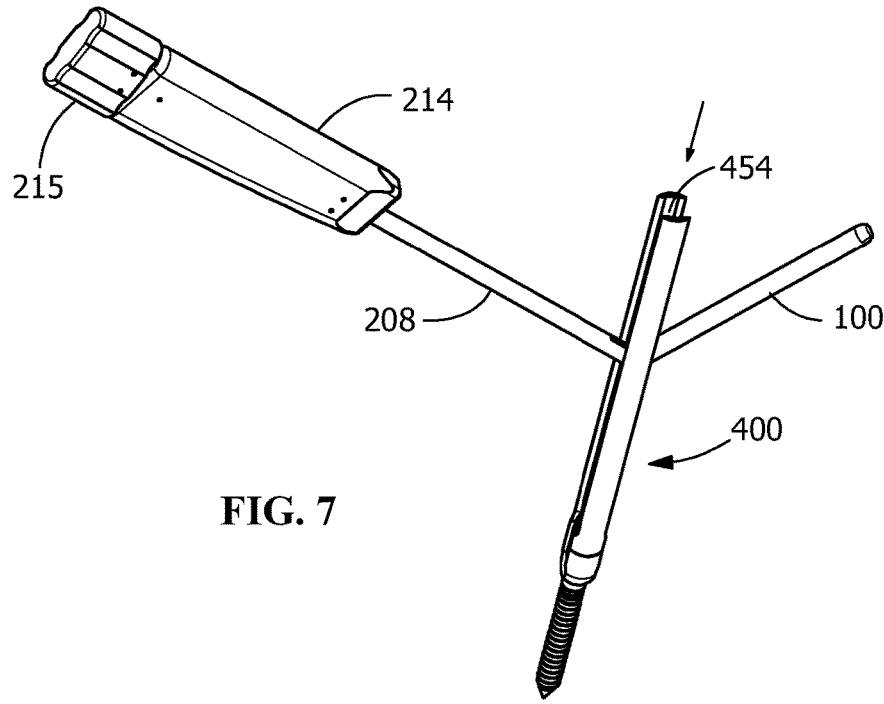
FIG. 7 shows a representative embodiment of the monoaxial screw assembly as shown in FIG. 4, with indicia demonstrating one approach for insertion of the rod into the central passage.
Figure 8:
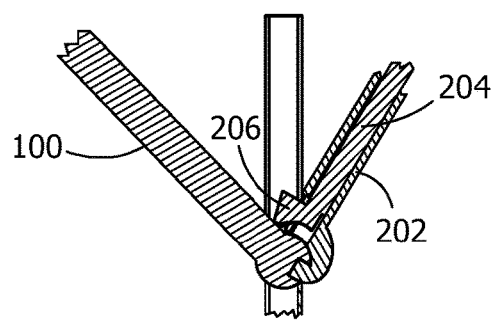
FIG. 8 shows an alternate close-up cross-sectional view of the monoaxial screw assembly as shown in FIG. 4.
Figure 11:
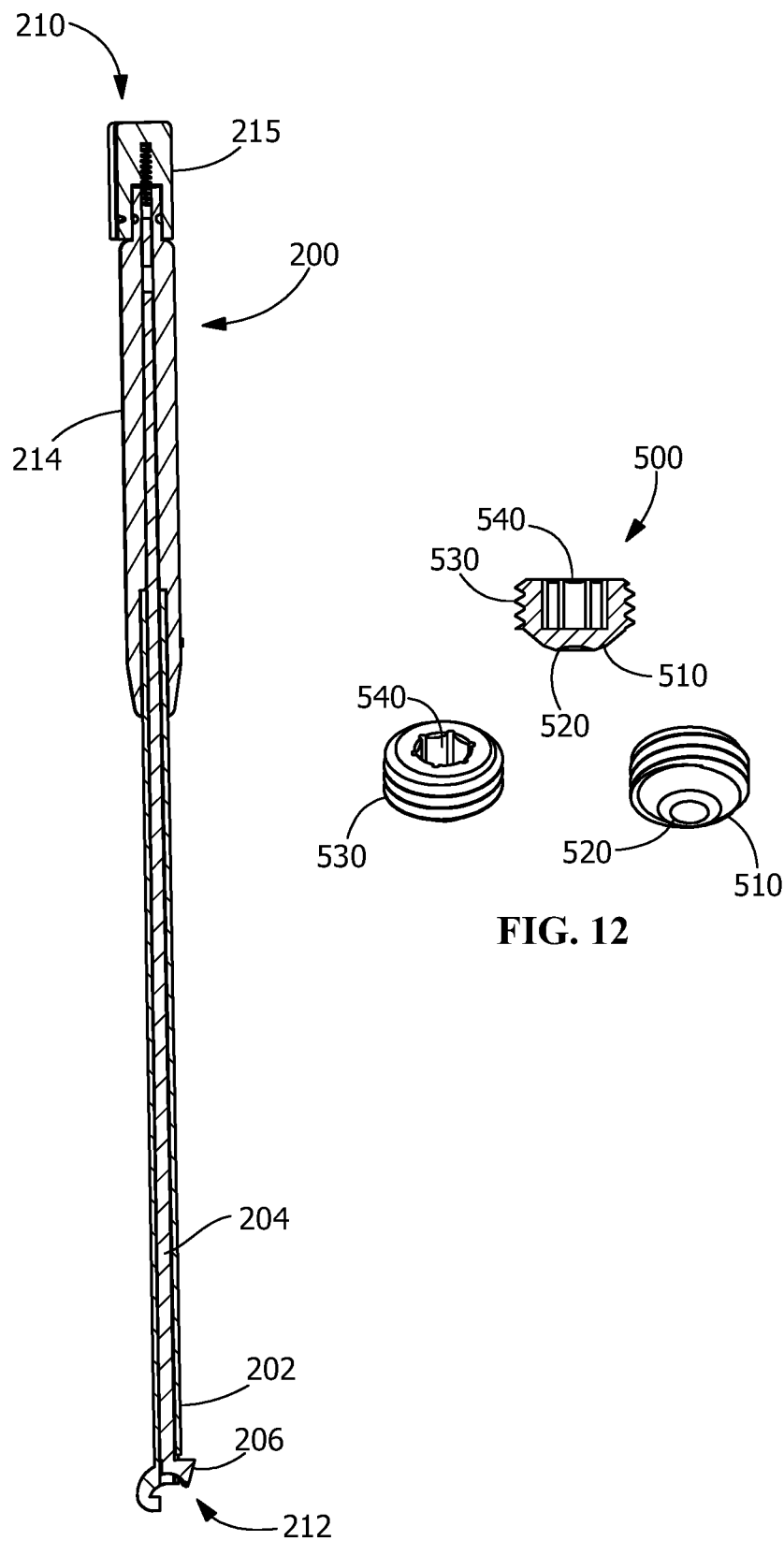
FIG. 11 shows, in a side cross-sectional view, of the inserter instrument demonstrating the two spherical head engagement features.

Referring now to FIGS. 7 and 11, in one embodiment the inserter tool 200 includes an elongate body 208, a handle 214 at a first end 210 of the elongate body 208, and the engagement projection 202 at the second end 212 of the elongate body 208. The engagement projection 202 is shaped and disposed to mate with the engagement recess 106 of the spinal stabilization rod 100. The retention projection 204 moves independently from the engagement projection 202, and includes at the second end 212 a locking projection 206. The position of the locking projection 206 is adjustable from the handle 214 by turning the actuating knob 215 that reciprocates the retention projection 204 within and along the axis of the elongate body 208 of the engagement projection 202 to alternately engage and disengage the locking projection 206 from contact with the rod head 104.

The engagement projection 202 of the inserter tool 200 may engage with the engagement recess 106 of the spinal stabilization rod 100 in any suitable manner. In one embodiment, the engagement recess 106 is disposed to mate with the retention projection 204 of the inserter tool 200, and a portion of the head 104 is disposed to mate with the locking projection 206 of the inserter tool 200.

Referring now to FIG. 4, in one embodiment, a monoaxial fixation screw assembly 400 for surgical implantation includes a spinal stabilization rod 100 and a first spinal stabilization monoaxial screw assembly 402. Referring now to FIG. 6, the first spinal stabilization monoaxial screw assembly 402 includes a first fixation screw 404, a receiver body 406, opposing slats 452 that extend from the receiver body 406, and a generally cylindrical compression component 500. The fixation screw 404 includes a shank 410 having a thread 412 arranged and shaped to engage bone. The receiver body 406 includes an aperture having a generally U-shaped conformation 414, a base 416, and opposing sidewalls 418 having a threaded portion 420. The generally cylindrical compression component 408 includes a threaded surface 422 disposed and arranged to engage with the threaded portion 420 of the opposing sidewalls 418 of the receiver body 406 and compress against the spinal stabilization rod 100, compressing the spinal stabilization rod 100 into the seat 440 base 416. The first spinal stabilization monoaxial screw assembly 402 may be a uniaxial screw assembly in which the first receiver body 406 is rotatable relative to the shank 410 in only one axis of rotation, is fixed such that the receiver body 406 cannot move relative to the shank 410, thus, the fixation screw 404 and the receiver body 406 may be a unitary article or a non-unitary assembly.

The seat 440 includes at least one curved surface forming a seat 440 that is complementary with a curved contact surface 112 on a contacted spinal stabilization rod 100 head 104 to permit rotation of the rod 100 head 104 therein. In accordance with some embodiments, the curved seat 440 is generally spherical and concave in shape and cooperates with the curved contact surface 112 of the rod 100 head 104 to enable rotation in multiple planes. It will be appreciated that other non-contacting surfaces of the rod 100 head 104 and of the receiver body 406 may or may not have a curved surface. In some particular embodiments, the seat 440 has a concave generally spherical seat that is bounded on opposing sides within the receiver body 406 by flats that do not contact the head 104 of the rod 100 and do not limit its articulation. In other particular embodiments, the seat 440 has a concave generally spherical shape that is bounded on opposing sides within the receiver body 406 by flats to form a slot that may in some embodiments contact the head 104 of the rod 100 to limit its articulation to a single plane, whereby, insertion of a rod 100 head 104 having a complimentary shape into the slot may limit the rotational articulation of the head 104 within the seat 440 to a single plane. It will be appreciated that in the various embodiments, the seat 440 for the rod 100 head 104 may be spherical, or it may have a combination of curved and non-curved surfaces, wherein the contact surface for rotational articulation of the rod head 104 in the seat 440 is curved, and in some examples, is spherical.

According to the foregoing description, in one embodiment the inventive monoaxial fixation screw assembly 400 according to the disclosure includes a monoaxial screw assembly 402, and a compression component 500 engageable within a receiver body 406 of the monoaxial screw assembly 402 to secure the spinal stabilization rod 100 therein. According to the various embodiments, the monoaxial fixation screw 402 includes a shank 410 that extends from a receiver body 406. The receiver body 406 and shank 410 are fixedly engageable with one another along a shared central axis. The shank 410 is threaded to engage bone and the receiver body 406 has opposing sidewalls, a generally U-shaped conformation, sidewall apertures, threads on at least a portion of an interior side of the sidewall, and a seat 440 for receiving the stabilization rod head, the seat including at least one spherical surface. The fixation screw also includes affixed elongate opposing slats 452, each having a first end that that terminates at a proximal slat edge wherein the opposing slates 452 form an opening into a central passage 454, and each having a second end that is releasably engageable with the receiver body 406 of the monoaxial fixation screw.

In accordance with the various embodiments, the shank, receiver body and elongate opposing slats 452 form a unitary structure that is monolithic, such as for example the embodiment shown in FIG. 6. According to such embodiments, the opposing slats 452 each comprises a feature such as a pre-etched score 480 or cut line to facilitate removal of the slats using a suitable tool once the assembly is fully affixed to the bone and the surgical procedure is complete. It will be appreciated by one of ordinary skill in the art that other means may be employed for achieving removal of slats, and disclosure is not limited to the use of pre-attached scoring or cut lines.

In other embodiments, the monoaxial fixation screw comprising the receiver body is unitary with the shank and the slats are part of a separately engageable elongate tower structure (not shown). In such embodiments, the receiver body 406 includes at least one emplacement (not shown) shaped and disposed to receive the pair of opposing slats, wherein the slats are not integral with the receiver body 406, and may be removably attached and are embodied as separate slats or in a tower construct that comprises opposing slats. According to such embodiments, the tower and the receiver body 406 include means for releasable inter-engagement.

One of ordinary skill in the art will appreciate that a variety of fixation screws are known with adaptations for engagement with insertion towers, and such features are generally suitable for enabling the inter-attachment of a tower and receiver bodies for each of the inventive assemblies of monoaxial fixation screw assembly 400 and pivoting screw assembly 300 according to the disclosure. Likewise, one of ordinary skill in the art will appreciate that a variety of fixation screws are known with adaptations for detachment of integrally formed slats, and such features are generally suitable for enabling the detachable slats and receiver bodies for each of the inventive assemblies of monoaxial fixation screw assembly 400 and pivoting screw assembly 300 according to the disclosure.

Fixation Assemblies Including a Spinal Stabilization Rod

The assembly also includes a spinal stabilization rod 100, and a generally cylindrical compression component 500 configured to engage a portion of the seat 440 of the receiver body and be complimentarily received therein. The spinal stabilization rod 100 has a head 104 that includes at least one curved contact surface 112 and at least one engagement recess 106 engageable with an inserter tool 200. The compression component 500 has a contact surface 520 for compressible engagement with the stabilization rod head and a peripheral edge having on at least a portion of its peripheral edge with threads 530 that are engageable within the seat 440 of the receiver body of the monoaxial fixation screw. The spinal stabilization rod 100 is sized for insertion through the central passage 454 between elongate opposing slats 452 and opposing sidewalls 418 for extension through at least a portion of aperture formed thereby and having a generally U-shaped conformation 414 for engagement of the stabilization rod head within the receiver body seat. The compression component 500 is configured to compress the head of the spinal stabilization rod 100 into the seat 440 of the receiver body 406 to lock the position of the spinal stabilization rod 100 relative to the monoaxial screw assembly 402.

It will be appreciated that the generally U-shaped conformation 414 of the apertures in the receiver body relative to the stabilization rod conform with what is conventional in the art for fixation screws, a key inventive feature being the engagement of the rod with the receiver body through a spherical surface that is not constrained within the U-shaped seat as it would be in a conventional fixation screw. Thus, in contrast with conventional designs, herein the spinal stabilization rod 100 is not secured by retention in a pair of opposing U-shaped apertures in the screw head (i.e., a tulip head) along a fixed axis defined by the U-shaped apertures; thus, the instant invention provides a seat for the rod head such that only the shaft portion of the rod is passed through the U-shaped aperture on one side of the fixation screw 404 to allow additional degrees of rotation of the spinal stabilization rod 100 relative to the fixation screw that cannot be achieved with assemblies in the known art.

It will be appreciated that embodiments including a spherical head engageable with a spherical seat provide the maximal opportunity for rotational motion within the receiver body of the fixation screw. Thus, in embodiments wherein the stabilization rod head is non-spherical and comprises a spherical surface and at least one flat that are complimentary with one or more flats in the seat, the ranges of motion will be more limited.

Figure 9:
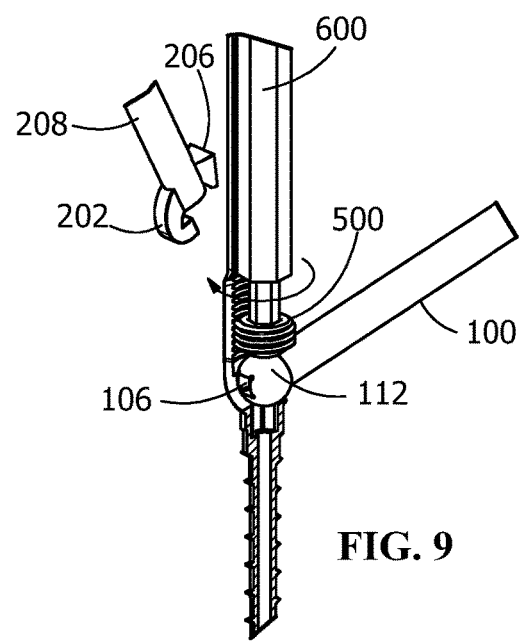
FIG. 9 shows an alternate close-up partial cross-sectional view of the monoaxial screw assembly as shown in FIG. 4, showing the compression component in communication with the driver for compression of the spherical head in the seat of the fixation screw receiver body.
Figure 10:
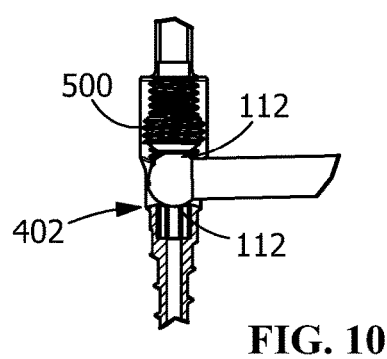
FIG. 10 shows an alternate close-up partial cross-sectional view of the monoaxial screw assembly as shown in FIG. 4, showing the compression component and the spherical head in a locked configuration in the seat of the fixation screw receiver body.

Referring now to FIG. 7 and FIG. 9, in accordance with the various embodiments, the engagement feature or features are configured to enable engagement of an inserter tool 200 therewith for releasably locked engagement whereby the spinal stabilization rod 100 is securely fixed to the inserter tool 200 in one configuration, and then can be released by actuation of the inserter tool 200 to release the spinal stabilization rod 100 upon placement within the receiver body 406 of the monoaxial screw assembly 402. Again, with reference to FIG. 7, the engagement recess is positioned to allow retention of the spinal stabilization rod 100 on the inserter tool 200 as the spinal stabilization rod 100 is passed through the opposing slats 452 of the monoaxial screw assembly 402, and further retained thereon once the spinal stabilization rod 100 is in the seat 440 of the receiver body 406 to thereby allow for contact with a compression component 500 passed through the opposing slats 452 and into lockable engagement with the stabilization rod head 104.

In some embodiments, one or more of the spinal stabilization rod 100 shaft 102 and the head 104 include surface texturing features to enhance purchase with assembly components when locked therein. Thus, in accordance with some possible embodiments, the stabilization rod head may include concentrically oriented rings or scoring on at least the portion of the head that is to be contacted by the compression member. In some embodiments, there is no surface texturing. In general, a variety of texture means are known in the fixation screw art in connection with fixation of heads of screws, and one of ordinary skill would select from among such features as desired to enhance purchase between the stabilization rod and one more assembly components.

Also, according to the foregoing description, in the various embodiments, the compression component 500 is configured to compress the head 104 of the spinal stabilization rod 100 into the seat 440 of the receiver body 406 to lock the position of the spinal stabilization rod 100 relative to the monoaxial screw assembly 402, and has a generally cylindrical shape that is configured to engage a portion of the seat 440 of the receiver body and be complimentarily received therein.

Referring again to FIG. 12, the compression component 500 includes on a rod contact face 510 a contact surface 520 for compressible engagement with a curved contact surface 112 of the stabilization rod head 104, a peripheral edge with threads 530 having on at least a portion of its surface threads that are engageable within the seat 440 of the receiver body 406 of the monoaxial fixation screw 404, and on a face that is opposite the spinal stabilization rod head 104 contact surface 520 the compression component comprises a driver recess 540. As depicted in the representative embodiment shown in FIG. 12, the rod contact face 510 has a convex shape that tapers to a contact surface 520 that comprises a concave recess with a spherical contour. In some such embodiments, the taper is frusto conical. The contoured surface enables engagement with a spherical surface on the head of the stabilization rod, and the tapered shape permits enhanced rotational freedom of the head. Of course, in alternate embodiments the contact surface may be other than tapered. In some embodiments, the driver engagement feature comprises a recess that can receive a hex driver, or any other driver features known in the art.

Figure 12:
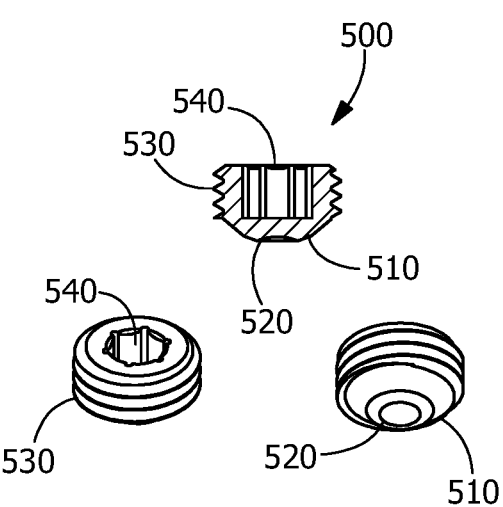
FIG. 12 shows in perspective top and bottom and side cross-sectional views a representative embodiment of a compression element for use in a monoaxial screw assembly according to the disclosure.
Figure 13:
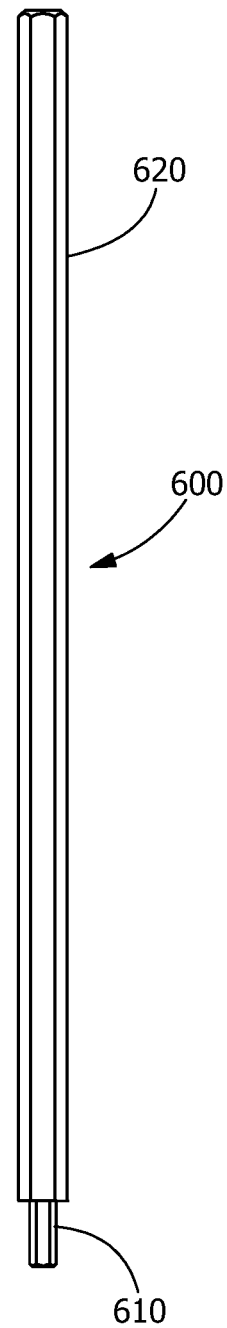
FIG. 13 shows a representative embodiment of a hex driver inside for engagement with one or both of a fixation screw and compression element.

In some embodiments, the compression component 500 is a unitary part as depicted in FIG. 12. In some alternate embodiments, the compression component comprises a washer that has a face shaped to engage with a surface of a rod head 104 and a separate compression element 500. According to some such embodiments, the washer may have a convex face that tapers to frusto conical, and comprises a concave recess with a spherical contour. In yet other such embodiments, the face of the washer may be other than frusto conical, and may in some instances be planar with a center bore or concavity for engagement with a spherical or other curved surface 112 on the head 104 of the stabilization rod 100.

According to the various embodiments of the compression component, the threaded portion 420 may comprise threads that may be single leads, double leads, fixed screw leads, and variable screw leads adapted for inter-engagement with the threaded interior sidewall and or with threads on the walls of the opposing slats that are proximal to the receiver body 406, or on the interior wall within the receiver body 406. In some embodiments, the bone anchor is adapted for insertion into cancellous bone, specifically the pedicle of a vertebra.

Generally, the foregoing paragraphs pertaining to fixation assemblies that include a spinal stabilization rod and the compression component also pertain to embodiments of the pivoting screw assembly 300 as described herein below, wherein the references made herein above to the components of the monoaxial fixation screw assembly 400 are replaced with references to those features that are analogous within the embodiments of the pivoting screw assembly 300 as described herein below. Thus, for the avoidance of doubt, each of the compression component 500 and spinal rod 100 described herein may be employed with any one of the inventive pivoting screw assembly 300, monoaxial fixation screw assembly 400 and conventional fixation screw assemblies.

Further, in accordance with the various embodiments herein, the opposing slats of one of the monoaxial fixation screw assembly 400 and pivoting screw assembly 300 are characterized as defining a central passage from a proximal opening between the slats and into the receiver body of the screw assembly, wherein the central passage has a generally circular cross section having a circumference that is defined by generally arcuate proximal edges of each of the pair of opposing slats. In accordance with the various embodiments, the slats have a width dimension along their long axis that is either continuous or tapers. In some embodiments, the slats have a continuous width from their junction with the receiver body up to their proximal edges. In other embodiments, the slats have a variable width from their junction with the receiver body up to their proximal edges, wherein in some embodiments each slat tapers towards its proximal edge such that the width is greater toward the receiver body and narrower towards the proximal edge. In some embodiments the slats taper adjacent the junction and towards their proximal edges. In some particular embodiments, the slats taper from the juncture between the upper edge of the threaded portion of the receiver body sidewalls, corresponding with the juncture at which the slats are joined or joinable with and detachable from the receiver body sidewalls according to the embodiments described herein. Thus, in some embodiments, the junction may be at a score.

In some embodiments, the opposing slats are tapered from the junction to a proximal edge. In some particular embodiments, the taper is fixed along the full length of the slat, and in some embodiments, the taper is gradual wherein the taper is greater at the proximal edges of the slats. In the various embodiments, the circumferential dimension of the two opposing slats as a percentage of the circumferential dimension of the central passage (the percent slat circumference) ranges from 10% to about 99%. In some particular embodiments, the percent slat circumference is no more than 60% of the circumference dimension of the central passage, the remainder of the circumference defined by opposing gaps between the opposing slats. In some particular embodiments, the percent slat circumference may be represented by the portion of the central passage circumference at the proximal end of the central passage (the proximal slat edges). According to such embodiments, the portion of the central passage circumference defined by the proximal edges of the opposing slats may be from as little as 10% to as much as 99%. And, more particularly, the portion of the central passage circumference defined by the proximal edges of the opposing slats may be from about 10% and up to about 60%, within a range from about 10% to about 60%, and in some embodiments from about 10% and up to about 55%, and in some embodiments from about 15% and up to about 50%, and in some embodiments from about 20% and up to about 50%, and in some embodiments from about 25% and up to about 45%.

With reference to certain embodiments as disclosed herein and shown in the drawings, the portion of the central passage circumference defined by the proximal edges of the opposing slats is from about 30% to about 35%.

Likewise, according to the various embodiments, the portion of the central passage circumference defined by the opposing slats along the at least a portion of the length of the passage comprises from as little as 10% to as much as 99%. And, more particularly, the portion of the central passage circumference defined by the opposing slats along at least a portion of the length of the passage comprises from about 10% and up to about 60%, within a range from about 10% to about 60%, and in some embodiments from about 10% and up to about 55%, and in some embodiments from about 15% and up to about 50%, and in some embodiments from about 20% and up to about 50%, and in some embodiments from about 25% and up to about 45%.

With reference to certain embodiments as disclosed herein and shown in the drawings, the portion of the central passage circumference defined by the opposing slats is from about 30% to about 35% along the length of the slats from just proximal to the threaded portion of the opposing walls and up to the slat proximal edges.

In use, the opposing slats are engaged within a grip handle as further described herein, whereby the position and stability of the slats are fortified by the grip handle, and enable a surgeon to grasp and manipulate the affixed assembly by either rotation or pivoting within one or more of the sagittal and transverse planes relative to the spine, as described herein. It will be appreciated that certain benefits are derived from design wherein the amount of material forming the slats is minimized and the gaps between are maximized.

Pivoting Fixation Screw Assembly

Referring to FIGS. 14-18, in one embodiment, a pivoting screw assembly 300 for surgical implantation includes a fixation screw 302, a receiver body 304, and a generally cylindrical compression component 306.

Figures 14, 15:
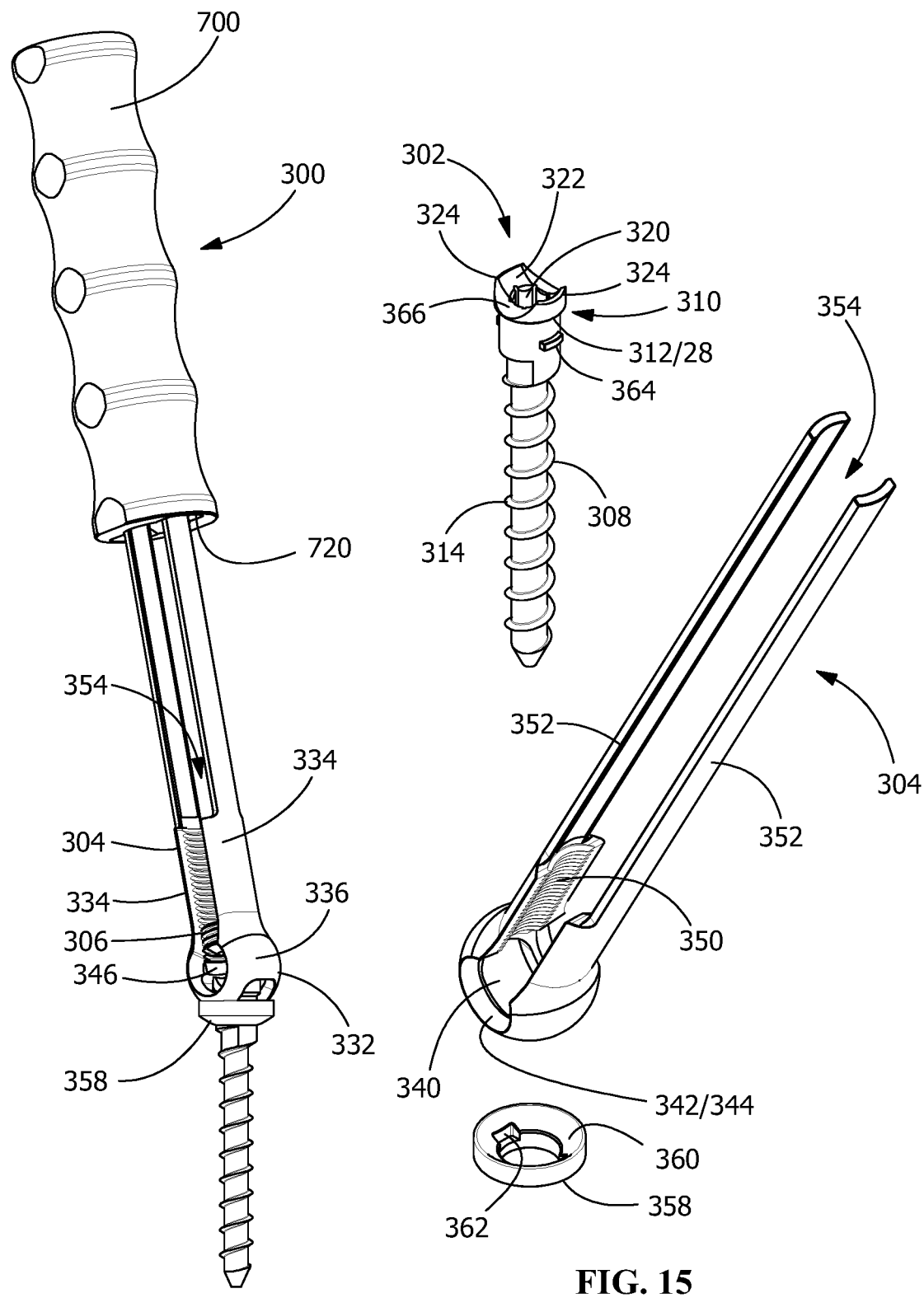
FIG. 14 shows a perspective view of an embodiment of the pivoting screw assembly.
FIG. 15 shows an alternate view of the pivoting screw assembly of FIG. 14, shown disassembled.

Referring again to FIGS. 14-18, in one embodiment, the fixation screw 302 includes a distally oriented shank 308, a proximally oriented screw head 310, and a tapered surface 312. Referring now to FIG. 15, the shank 308 includes a thread 314 arranged and shaped to engage bone. The screw head 310 includes a tapered surface 312, a drive recess 320, and a cradle 322 that is disposed proximally and extending from the screw head 310 and away from the shank 308. In some embodiments, as is depicted in the figures, the cradle 322 includes at least two opposing arms 324 defining a curved cradle 322 surface shaped and disposed to receive and support a spinal stabilization rod 100. The tapered surface 312 joins the screw head 310 and the shank 308. The tapered surface 312 may include any suitable taper, including, but not limited to, a linear taper 328, a curved taper (not shown), or a combination thereof.

Referring again to FIG. 14 and FIG. 15, in one embodiment, the receiver body 304 is adapted for engagement with the fixation screw 302, and includes an aperture having a generally U-shaped conformation 330, a base 332, and opposing sidewalls 334. The base 332 includes a curved exterior surface 336, a sidewall interior surface 348 having a through slot 340 for receiving the shank 308, and a seat 342 with a curved surface 344 for contacting the tapered surface 312 of the fixation screw 302. The opposing sidewalls 334 extend from the base 332, and include opposing flats 346 on a sidewall interior surface 348 adjacent to the base 332. The opposing sidewalls 334 further include a threaded portion 350 proximal to the opposing flats 346. The base 332 and the opposing sidewalls 334 are shaped and disposed to receive the spinal stabilization rod 100 in contact with the cradle 322 of the screw head 310.

Referring now to FIG. 15, in one embodiment, the receiver body 304 includes a pair of opposing slats 352 extending from above the threaded portion 350 away from the seat 342. The pair of opposing slats 352 defines a central passage 354. The pair of opposing slats 352 may be attached to the receiver body 304 in any suitable manner, including, but not limited to being integrally formed with the receiver body 304, joined to the receiver body 304, welded to the receiver body 304, affixed to the receiver body 304, or combinations thereof. In one embodiment, the pair of opposing slats 352 is removably attached to the receiver body 304. In further embodiments, the pair of opposing slats 352 include a score 380 for removal from the receiver body 304. In another embodiment, the receiver body 304 includes at least one emplacement (not shown) shaped and disposed to receive the pair of opposing slats 352, wherein the slats are not integral with the receiver body 304, and may be removably attached and are embodied as separate slats or in a tower construct that comprises opposing slats.

Referring now to FIG. 16, in one embodiment, the generally cylindrical compression component 306 includes a threaded surface disposed and arranged to engage with the threaded portion 350 of the opposing sidewalls 334 of the receiver body 304 and compress against the spinal stabilization rod 100, compressing the spinal stabilization rod 100 into the cradle 322 of the screw head 310. It will be appreciated that the compression component 500 shown in FIG. 12 may be used, or another set-type screw may be selected from the known art.

Figure 18:
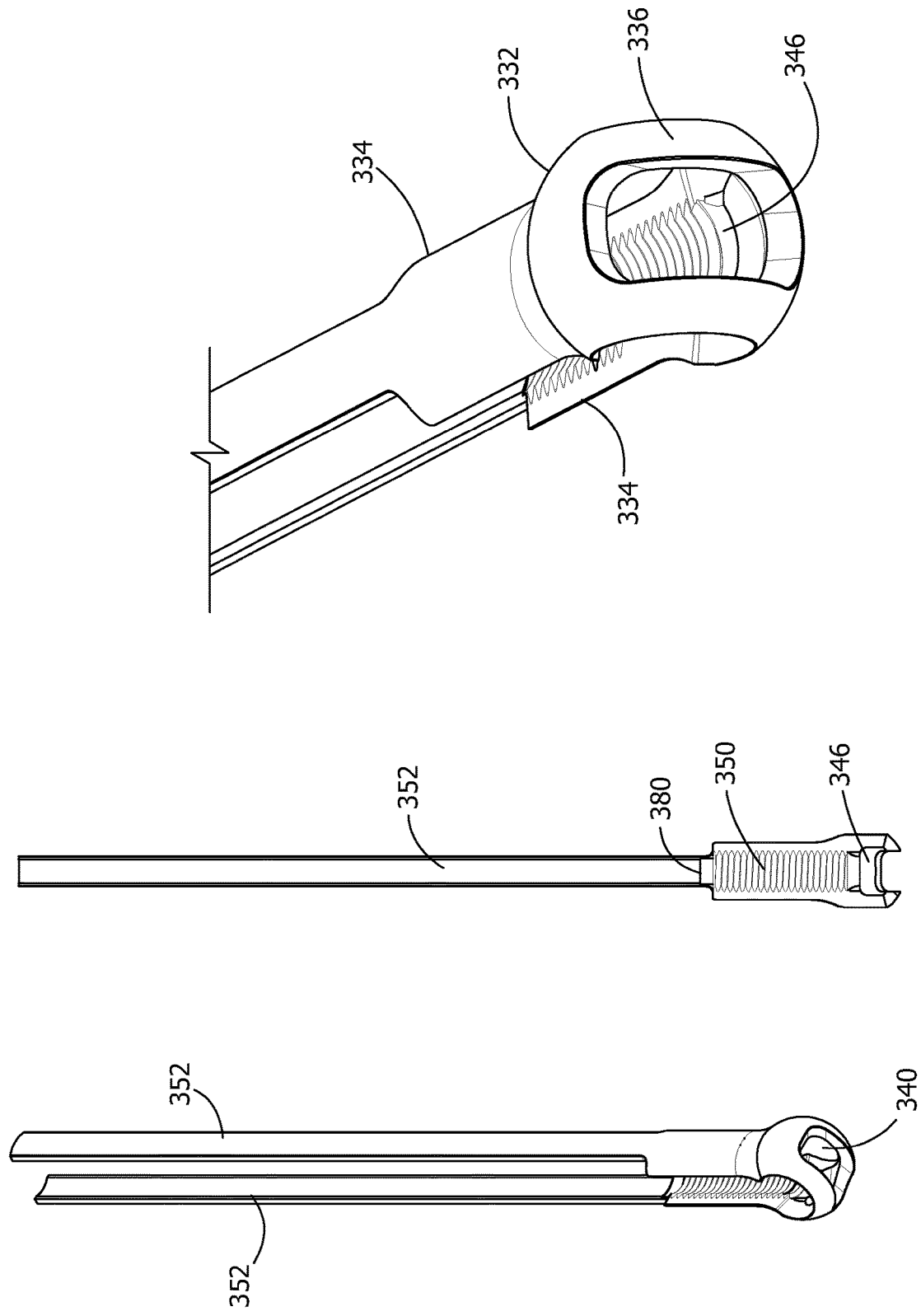

Referring now to FIG. 18, in one embodiment, two or more surfaces selected from the curved exterior surface 336 of the base 332 and the curved surface 344 of the seat 342 of the base 332 include an essentially common curvature. As used herein, "essentially common curvature" indicates that any differential between the curved exterior surface 336 and the curved surface 344 is less than about 10%, alternatively less than about 5%, alternatively less than about 1%, alternatively less than about 0.1%.

Referring again to FIG. 18, in one embodiment, as assembled, the tapered surface 312 of the screw head 310, and the curved surface 344 of the seat 342 of the base 332 cooperate to allow pivotal movement of the receiver body 304 on a single axis of rotation aligned with the essentially common curvature, and the opposing flats 346 restrict the pivotal motion of the receiver body 304 by contacting the opposing arms 324 of the screw head 310.

Referring again to FIG. 15, the pivoting screw assembly 300 may include a footing 358, having a curved support surface 360 shaped and disposed to support the curved exterior surface 336 of the base 332. In one embodiment, the curved support surface 360 of the footing 358 includes the essentially common curvature along with the curved exterior surface 336 of the base 332 and the curved surface 344 of the seat 342 of the base 332.

In one embodiment, the footing 358 includes at least one clocking alignment recess 362, and the fixation screw 302 includes at least one clocking alignment projection 364, arranged and disposed to engage with the at least one clocking alignment recess 362 when assembled. The engagement of the at least one clocking alignment recess 362 and the at least one clocking alignment projection 364 may fix the rotational alignment of the fixation screw 302 and the footing 358 relative to one another in the plane of the engagement.

Referring again to FIG. 15, the screw head 310 may further include a plurality of contoured surfaces 366 sloping away from the cradle 322 toward the tapered surface 312. The plurality of contoured surfaces 366 may include any suitable contours, including, but not limited to, bevels, chamfers, curves, or combinations thereof. The contoured surfaces 366 support a rod that is inserted through the generally U-shaped conformation 330 of the receiver body 304 where the angulation of the rod precludes it from resting on the cradle 322. And referring yet again to FIG. 15, the curved surface 344 of the seat 342 of the base 332 includes a slope that is oriented away from the through slot 340. In some embodiments, as depicted in the drawings, the slope matches the slope of the contoured surface 366 of the screw head 310.

According to the foregoing description, in an embodiment, the pivoting screw assembly 300 includes a fixation screw 302, the fixation screw 302 including a threaded shank 308 and at least partially screw head 310. In some embodiments, the screw head 310 has opposing flats (not shown). Also included is a receiver body 304 with a receiving seat 342 for receiving the screw head 310 of the fixation screw 302, the seat 342 configured with a through slot 340 with a curved surface 344. The seat 342 has a through slot 340 that allows the shank 308 to pass thorough the seat 342, sized to retain the head and bounded by opposing flats 346 on the sidewalls interior surface 348 and below a threaded portion 350 to allow pivoting within a limited range. The implants include a footing 358 that may be welded to the shank 308, acting as a "cap", constraining the receiver body 304 from moving up or down the shank long axis.

When placed into the through slot 340 of the seat 342 of the receiver body 304, the shank 308 has 2 degrees of freedom. The first degree of freedom is pivotal motion (i.e., rotation about a pivot axis that is perpendicular to the axis of the screw shank and that is oriented along the longitudinal axis of the spine when the assembly 300 is implanted in a vertebra) within the through slot 340 +/−90°. The pivotal motion is from at least about +/−5° and up to about +/−90°, within a range from about +/−10° to about +/−60°, and in some embodiments from about +/−10° to about +/−45°, and in some embodiments from about +/−10° to about +/−30°, and in some embodiments from about +/−10° to about +/−25°, and in some embodiments from about +/−10° to about +/−15°. The second degree of freedom is axially (around the shank long axis), wherein rotation allows the receiver body 304 to rotate and to pivot relative to the shank 308 during and after insertion of a rod shank in bone. The axial rotation is from at least about +/−1° and up to about +/−90°, within a range from about +/−1° to about +/−90°, and in some embodiments from about +/−1° to about +/−75°, and in some embodiments from about +/−1° to about +/−60°, and in some embodiments from about +/−1° to about +/−45°, and in some embodiments from about +/−1° to about +/−30°, and in some embodiments from about +/−1° to about +/−15°, and in some embodiments from about +/−1° to about +/−10°, and in some embodiments from about +1-1° to about +/−5°, and in some embodiments from about +/−2° to about +/−4°. Thus, in various embodiments, the receiver body 304 can pivot up to about 90° and can rotate about the axis up to about 90°, each rotational and pivotal motion being relative to an essentially 0° position wherein the screw head 310 is centered within the through slot 340 and the axis of the central passage 354 is aligned with the axis of the screw shank 308.

Axial rotation of the screw within the through slot 340 allows the threads to be driven into bone without interference with the receiver body 304. The receiver central passage 354 is further adapted to receive there-through a stabilization rod that may be inserted along the axis for placement of its head 104 within the cradle 322 of the assembly, or a shaft 102 of a conventional or inventive spinal stabilization rod 100 may be inserted essentially transverse through the elongate opposing slats 352 and the generally U-shaped conformation 330 for placement of the spinal stabilization rod 100 through the screw 302 with the rod resting in the cradle 322.

In use according to some embodiments, one or more pivoting screw assembly 300 may be used together with one or more fixation components, including, optionally: one or more conventional spinal fixation assemblies (for example, screws typically used for implantation in the pedicles); one or more monoaxial fixation screw assembly 400, an elongate stabilization rod 100 having a head 104 that includes at least one curved surface 112. Placement of the pivoting screws adjacent to an inventive monoaxial fixation screw assembly 400 described herein above is particularly desirable to enhance the alignment of the rod within the retaining portions of each screw and to then use the conventional spinal fixation screw to maximize the ability of the surgeon to rotate or de-rotate the adjacent vertebra for optimizing sagittal balance. The assemblies disclosed herein when used together enable controlled rotation or de-rotation of adjacent vertebrae and fixation thereof to enhance sagittal balance.

Additional Features of Assemblies

The components of the surgical implant assemblies provided herein may be adapted with features specific to use in percutaneous procedures. Thus, in some embodiments, one or more of each of the fixation screws and compression components of the surgical implant system includes a guide wire aperture that is coaxial with the respective assemblies to permit percutaneous surgical access.

In use, the inventive assemblies may be employed together with conventional screw assemblies, such as the variety of fixation screw systems known in the art, to provide a system of assemblies for achieving spinal fixation and stabilization with enhanced sagittal balance in accordance with the surgical techniques as disclosed herein.

Referring now to FIG. 17, a handle grip 700 is shown. As seen in the various drawings, the handle grip 700 can be affixed to the elongate slat components of the inventive assemblies via slat engagement slots 720 that enable controlled engagement and stabilization of the slats for manipulation of the assemblies, such as for rotation of the monoaxial fixation screw assembly 400 to rotate or de-rotate adjacent vertebrae, or to affect pivotal rotation of the pivoting screw assembly 300. The handle grip 700 further includes a grip through hole 710 for passage through the handle grip 700 of various tools, such as drivers, and components such as rods and screws. The handle grip 700 as depicted includes surface shapes and features to enhance grasping and comfort of the user. It will be appreciated that in other embodiments, such features may be varied.

Referring again to FIG. 11, the systems according to the disclosure herein include instruments to facilitate manipulation of conventional fixation screws and set screw components, as well as inventive monoaxial fixation screws and compression components, such instruments including comprising a driver tool 600 having a driver feature selected from the group consisting of a hex driver, a Philips head screw driver, flat head screw driver, and a torx driver. Instruments also include a rod inserter tool 200, for example according to the embodiment shown in FIGS. 4, 7, and 11, the inserter tool 200 comprising an elongate body 208, at a first end 210 a proximal handle 214, at a second end 212 a distal engagement projection 202 and a distal locking projection 206, and an actuating mechanism for releasably engaging the distal engagement feature with an insertion tool recess on the stabilization rod head. As shown, the depicted embodiment includes a handle 214 with a proximal actuating knob 215 at the first end 210, an elongate body 208 and a pair of engagement legs one formed by the engagement projection 202 and one formed by the retention projection 204 which includes at its second end 212 a locking projection 206, wherein at least one leg is actuated to reciprocate along the long axis of the elongate body 208 to engage or disengage with the head of the stabilization rod.

It will be appreciated that other engagement mechanisms may be selected that enable releasable fixation with the rod head, and further that other actuation features may be utilized to drive reciprocation or other motion of an engagement feature into and out of engagement with the rod head. In use, the tool as affixed to the rod head enables controlled introduction of the rod into the fixation screw, either by passage transversely through the slats with the head of the rod passing within the central passage and the tool and the distal end of the rod, respectively, extending transversely through the generally U-shaped conformation. In other embodiments, the rod may be passed with its axis aligned with the central passage, whereby the elongate body of the tool is oriented first transverse to the slats and is rotated as the second terminus of the rod reaches the seat in the receiver body so that the rod is passed out of the generally U-shaped conformation upon rotation of the tool along an arc. In use, the tool also allows controlled rotational positioning of the rod when it is within the seat to enhance aligning and engaging the rod within a generally U-shaped conformation of an adjacent screw assembly.

Systems and Methods of Use

In some embodiments, the inventive monoaxial fixation screw assembly 400 including the spinal stabilization rod having a spherical head may be used with a conventional fixation screw (for example, mono or polyaxial type fixation screw) whereby upon provisional placement of the shaft portion of the rod within the conventional fixation screw, the vertebra into which the inventive assembly is affixed may be rotated/de-rotated to achieve the desired extent of distraction within the disc space followed by final locking of the rod into the conventional fixation screw.

In other embodiments, the inventive monoaxial fixation screw assembly 400 including the spinal stabilization rod having a spherical head may be used with the inventive pivoting screw assembly 300 hereof whereby the combination of the adjustability of the stabilization rod, and the pivotal motion of the screw assembly enhances the engagement of the rod between the two assemblies. The screw assembly can then be used as a fulcrum for rotation of the affixed vertebra.

A further benefit that can be realized by use of one or more of the inventive assemblies 300, 400 is an effective reduction in the torque to be placed on each of adjacent fixation screws to place a spherical headed stabilization rod into position within the receiving apertures in the adjacent screws, thereby diminishing the risk of bone failure or fracture and of screw failure. The derivative benefits realized include but are not limited to improved patient comfort and outcomes associated with optimized sagittal balance.

It will be appreciated that embodiments of the present invention are not limited to use in any approach for spinal surgery, and may be adapted for use, for example, in a transforaminal approach, among other spinal surgical approaches and orientations and other surgical sites within the body.

Surgical Technique

Also in accordance with the disclosure is a surgical technique for performing a procedure on the spine of a patient utilizing the surgical instruments and implants hereof to enable controlled positioning and alignment of a spinal stabilization rod between adjacent fixation screws, and enhanced rotation/de-rotation of adjacent vertebrae for long term fixation and stabilization. Below and in the drawings a representative surgery involving fixation in the pedicles is described. Of course, other surgical procedures and implantation into other bony structures is possible with the inventive assemblies, and the examples are not limiting in any way to use in spinal pedicles.

Referring to FIG. 3, a schematic view shows successive configurations of spinal manipulation using one or more of conventional implants together with one or more of implants and instruments according to the disclosure in the context of a spinal construct, wherein in each represented configuration A, B and C, the techniques for implant placement and engagement, manipulation by compression/rotation, and implant fixation by locking are achieved. According to the method of treatment, a surgical stabilization system is provided, the system including at least four fixation screw assemblies, at least one monoaxial fixation screw assembly 400, the remaining assemblies selected from conventional, monoaxial fixation screw assembly 400 and pivoting screw assembly 300, sequentially prepping the bone and securing each assembly therein.

Prior to initiating the procedure, the surgeon will determine both the size and number of spinal implants that may be needed (if any), and the degree of correction that may be required for the patient along the axis of the spine to address hyper lordosis or hyper kyphosis within the region(s) to be treated. The surgeon may select one or more spinal implant interbody devices for each of the vertebral disc spaces intended for treatment, for example, the surgeon may select one or more lordotic implants that will introduce an enhanced forward curvature to the spine in the instance of a defect causing, for example, kyphosis in the lumbar spine. Further selection from among the inventive assemblies hereof will enable the surgeon to control the extent of vertebral rotation/de-rotation along the sagittal plane to establish the extent of lordosis or kyphosis intended for the treated area.

In accordance with known and customary surgical procedures, the target vertebrae are prepared for any one of conventional and inventive fixation assemblies. Pilot holes are created using drill bits and a probe or other suitable instruments for forming a hole and confirming trajectory to avoid breach. Screws are introduced into the established pre-drilled holes using conventional drivers selected from hex and other driver types. In some common examples in the art involving implantation in pedicles, at least two pairs of fixation screw assemblies are used for a single level (single disc space) procedure to stabilize the adjacent vertebra during healing/fusion. In accordance with such examples, the surgeon may select pairs of fixation screws exclusively from among the inventive assemblies hereof, or may combine one or both assemblies with a conventional fixation screw assembly. Selection for placement of the conventional fixation screw assemblies and of an embodiment of the inventive assemblies herein is made based upon the surgeon's determination of the most desirable adjustment to the spine.

As described above, placement of an inventive pivoting screw assembly 300 in a first vertebra that is positioned to engage with a monoaxial fixation screw assembly 400 in the adjacent vertebra is particularly desirable to enhance the alignment of the rod within the retaining portions of each screw to thereby maximize the ability of the surgeon to engage the two assemblies via the rod and then rotate or de-rotate the adjacent vertebra for optimizing sagittal balance. Of course, other combinations of the inventive pivoting and monoaxial screw assemblies are possible, and the described and depicted examples are nonlimiting.

In accordance with various embodiments, use of an assembly handle grip affixed to the elongate slat components of the inventive assemblies via slat engagement slots enable controlled engagement and stabilization of the slats for manipulation of the assemblies, such as for rotation of the monoaxial stabilization screw assembly to rotate or de-rotate adjacent vertebrae, or to affect pivotal rotation of the pivoting screw assembly. The handle grip through hole allows passage of various tools, such as drivers, and components such as rods and screws, thereby ensuring stable controlled positioning of the opposing slats during manipulation of the assembly components.

In some embodiments, one of the inventive assemblies according to the disclosure will be placed in the vertebral body that is most superior (cranial) relative to the adjacent vertebral body that bounds the disc space to be corrected. In some embodiments, the most superior place assembly is the inventive monoaxial fixation screw assembly 400.

In some embodiments, stabilization rods according to the disclosure may traverse one or two or more levels or disc spaces. In some embodiments, the stabilization rods may traverse only a single level. Thus, in some embodiments wherein multiple levels are to be stabilized, surgical implant systems comprising conventional implant screws include sufficient conventional assemblies for the total number of target vertebrae minus one. In one example, for a two-level procedure, fixation screw assemblies would typically be employed for three vertebral bodies, and thus, in one example, one pair of conventional assemblies may be selected and two each of the inventive stabilization rod assembly and inventive pivoting screw assembly may be selected. In another example, two inventive stabilization rod assemblies may be selected for use with two pairs of inventive pivoting screw assemblies. And in yet another example, two inventive stabilization rod assemblies may be selected for use with two pairs of conventional fixation screw assemblies. Rod length will be selected based upon the distance between the superior and inferior most vertebra to be targeted, and the dimensions of the rod head will be selected based upon the dimensions of the screw selected to match the spinal anatomy.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The general inventive concepts may be embodied in different forms and should not be construed as limited to the embodiments set forth herein. Rather, these embodiments are provided so that this disclosure will be thorough and complete, and will fully convey the scope of the general inventive concepts to those skilled in the art.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

"Patient" is used to describe an animal, preferably a human, to whom treatment is administered, including prophylactic treatment with the compositions of the present invention. "Concave" is used herein to describe an indented surface without reference to the specific shape of the indented surface. As non-limiting examples, the concave face may be tubular with a round cross section, oval cross section, square cross section, or rectangular cross section.

"Stabilization rod" is used herein to refer to a device used to connect a plurality of bone screws together as is known in the art. This includes, without limiting the definition, rods, cables, bars, and wires.

Anatomical references as used herein are intended to have the standard meaning for such terms as understood in the medical community. For example, the application may include reference to the following terms: "cephalad," "cranial" and "superior" indicate a direction toward the head, and the terms "caudal," "caudad" and "inferior" indicate a direction toward the feet. Likewise, the terms "dorsal" and "posterior" indicate a direction toward the back, and the terms "ventral" and "anterior" indicate a direction toward the front. And the term "lateral" indicates a direction toward a side of the patient. The term "medial" indicates a direction toward the mid line of the patient, and away from the side, the term "ipsilateral" indicates a direction toward a side that is proximal to the operator or the object being referenced, and the term "contralateral" indicates a direction toward a side that is distal to the operator or the object being referenced. More specifically with respect to the directional movement of an implant according to the methods of the disclosure, sideways refers to the general direction of movement within the disc space between the endplates from the position of the inserted instruments toward one or the other of the contralateral and ipsilateral portions of the disc space. For example, in the case of a TLIF procedure, such sideways motion will generally be in a medial direction relative to the disc space. Though in other types of surgical access, particularly within the spine, sideways movement may be either medial or lateral relative to the disc space, and in other surgical contexts sideways is away from the initial position of the implant. Further, with respect to the movement of an implant by action of the surgical instruments, the movement may also be rotational, wherein the action of the instruments directs the implant sideways and in a rotational or pivotal motion. More generally, all terms providing spatial references to anatomical features shall have meaning that is customary in the art.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as may be described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more or fewer images, from more or fewer perspectives, may be collected.

One of ordinary skill will appreciate that references to positions in the body are merely representative for a particular surgical approach. Further, all references herein are made in the context of the representative images shown in the drawings. Fewer or additional instruments, including generic instruments, may be used according to the preference of the operator. Moreover, references herein to specific instruments are not intended to be limiting in terms of the options for use of other instruments where generic options are available, or according to the preference of the operator.

Reference Numeral Key: 100—Spinal Stabilization Rod; 102—Shaft; 104—Head; 106—Engagement Recess; 108—First Terminus; 110—Second Terminus; 112—Curved Contact Surface; 118—Juncture; 120—Tapered Conformation; 200—Inserter Tool; 202—Engagement Projection; 204—Retention Projection; 206—Locking Projection; 208—Elongate Body; 210—First End; 212—Second End; 214—Handle; 215—Actuating Knob; 400—Monoaxial screw assembly; 402—Fixation Screw Assembly; 404—Fixation Screw; 406—Receiver Body; 408—Compression Component; 410—Shank; 412—Thread; 414—Generally U-shaped Conformation; 416—Base; 418—Opposing Sidewalls; 420—Threaded Portion; 440—Seat; 452—Opposing Slats; 454—Central Passage; 480—Score; 490—Driver Recess; 300—Pivoting Screw Assembly; 302—Fixation Screw; 304—Receiver Body; 306—Compression Component; 308—Shank; 310—Screw Head; 312—Tapered Surface; 314—Thread; 320—Drive Recess; 322—Cradle; 324—Opposing Arm; 328—Linear Taper; 330—Generally U-shaped conformation; 332—Base; 334—Opposing sidewalls; 336—Curved Exterior Surface; 340—Through Slot; 342—Seat; 344—Curved Surface; 346—Opposing Flats; 348—Sidewall Interior Surface; 350—Threaded Portion; 352—Opposing Slats; 354—Central Passage; 358—Footing; 360—Curved Support Surface; 362—Clocking Alignment Recess; 364—Clocking Alignment Projection; 366—Contoured Surface; 380—Score; 500—Compression Component; 510—Rod contact face; 520—Contact surface; 530—Peripheral Edge with Threads; 540—Driver Recess; 600—Driver; 610—Driver Head; 620—Driver Handle; 700—Grip; 710—Grip Through Hole; 720—Slat Engagement Slots.

While the disclosed embodiments have been described and depicted in the drawings in the context of the human spine, it should be understood by one of ordinary skill that all or various aspects of the embodiments hereof may be used in connection with other species and within any species on other parts of the body where deep access within the tissue is desirable.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary, or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A pivoting screw assembly for surgical implantation, comprising:
    a fixation screw, including:
        a threaded shank, and a head having a concave curved cradle that is shaped and disposed to receive, contact, and support a cylindrical stabilization rod, and a tapered surface that is adjacent to the threaded shank, the tapered surface including a linear taper, a curved taper, or a combination thereof, wherein the screw head further includes a plurality of contoured surfaces sloping away from the cradle toward the tapered surface, the plurality of contoured surfaces adapted to support the cylindrical stabilization rod and including contours selected from the group consisting of bevels, chamfers, curves, and combinations thereof;
    a receiver body adapted for engagement with the fixation screw having an aperture
    having a generally U-shaped conformation, and including
        a base that includes a curved exterior surface, an interior surface having a through slot for receiving the shank and a seat with a curved surface for contacting the tapered surface of the fixation screw; and
        opposing sidewalls extending from the base, the opposing sidewalls including interior and exterior surfaces, and including on the interior surfaces opposing flats adjacent to the base and a threaded portion proximal to the flats; and
    wherein the base and the opposing sidewalls are shaped and disposed to receive the spinal stabilization rod in contact with the cradle of the screw head inserted in the through slot, and
    wherein the curved exterior surface of the base and the curved surface of the seat of the base include an essentially common curvature.

2. The pivoting screw assembly of claim 1, further comprising a generally cylindrical compression component including a threaded surface disposed and arranged to engage with the threaded portions on the interior surfaces of the opposing sidewalls of the receiver body, the compression component shaped to contact and compress against a spinal stabilization rod in contact with the cradle of the screw head.

3. The pivoting screw assembly of claim 1, further comprising:
    a spinal stabilization rod including
        a shaft including a first terminus and a second terminus;
        a head disposed at the first terminus, the head including a curved contact surface; and
        an engagement recess disposed in the curved contact surface.

4. The pivoting screw assembly of claim 1, wherein the receiver body includes a pair of opposing slats extending from above the threaded portion away from the seat, the pair of opposing slats defining a central passage and a handle grip adapted to be affixed to the elongate slats via insertion of the slats into opposing engagement slots, the handle grip including a central through hole, wherein the opposing slats are removably attached to the receiver body.

5. The pivoting screw assembly of claim 4, wherein the central passage has a circumference that is defined by the pair of opposing slats, and wherein not more than 60% of the circumference includes combined circumferential edges of the pair of opposing slats, and at least 40% of the circumference is defined by gaps between the opposing slats.

6. The pivoting screw assembly of claim 4, wherein the pair of opposing slats is detachable from the receiver body opposing sidewalls and includes a score for removal from the receiving body.

7. The pivoting screw assembly of claim 1, further including a footing, the footing including a curved support surface shaped and disposed to support the curved exterior surface of the base, the curved support surface of the footing including the essentially common curvature.

8. The pivoting screw assembly of claim 1, wherein the plurality of contoured surfaces are adapted to support the cylindrical stabilization rod that is inserted through the generally U-shaped conformation of the receiver body where an angulation of the rod precludes the rod from resting on the cradle.

9. A pivoting screw assembly for surgical implantation, comprising:
    a fixation screw, including:
        a threaded shank, and a head having a concave curved cradle that is shaped and disposed to receive and support a cylindrical stabilization rod, and a tapered surface that is adjacent to the threaded shank, the tapered surface including a linear taper, a curved taper, or a combination thereof, wherein the screw head further includes a plurality of contoured surfaces sloping away from the cradle toward the tapered surface, the plurality of contoured surfaces adapted to support the cylindrical stabilization rod and including contours selected from the group consisting of bevels, chamfers, curves, and combinations thereof;
    a receiver body adapted for engagement with the fixation screw having an aperture having a generally U-shaped conformation, and including
        a base that includes a curved exterior surface, an interior surface having a through slot for receiving the shank and a seat with a curved surface for contacting the tapered surface of the fixation screw; and
        opposing sidewalls extending from the base, the opposing sidewalls including interior and exterior surfaces, and including on the interior surfaces opposing flats adjacent to the base and a threaded portion proximal to the flats; and
    wherein the base and the opposing sidewalls are shaped and disposed to receive the spinal stabilization rod in contact with the cradle of the screw head inserted in the through slot, wherein the curved exterior surface of the base and the curved surface of the seat of the base include an essentially common curvature, and wherein, as assembled, the curved exterior surface of the base, and the curved surface of the seat of the base, restrict rotation of the receiver body to a single axis of rotation aligned with the essentially common curvature and wherein the opposing flats limit the extent of pivotal movement of the receiver body.

10. A pivoting screw assembly for surgical implantation, comprising:

a fixation screw, including:
 a threaded shank, and a head having a concave curved cradle that is shaped and disposed to receive and support a cylindrical stabilization rod, and a tapered surface that is adjacent to the threaded shank, the tapered surface including a linear taper, a curved taper, or a combination thereof;

a receiver body adapted for engagement with the fixation screw having an aperture having a generally U-shaped conformation, and including
 a base that includes a curved exterior surface, an interior surface having a through slot for receiving the shank and a seat with a curved surface for contacting the tapered surface of the fixation screw; and
 opposing sidewalls extending from the base, the opposing sidewalls including interior and exterior surfaces, and including on the interior surfaces opposing flats adjacent to the base and a threaded portion proximal to the flats; and a footing, the footing including a curved support surface shaped and disposed to support the curved exterior surface of the base, the curved support surface of the footing including the essentially common curvature;

wherein the base and the opposing sidewalls are shaped and disposed to receive the spinal stabilization rod in contact with the cradle of the screw head inserted in the through slot, wherein the curved exterior surface of the base and the curved surface of the seat of the base include an essentially common curvature, and wherein the footing includes at least one clocking alignment recess, and the fixation screw includes at least one clocking alignment projection arranged and disposed to interlock with the at least one clocking alignment recess when assembled.

11. The pivoting screw assembly of claim 10, wherein the screw head further includes a plurality of contoured surfaces sloping away from the cradle toward the tapered surface, the plurality of contoured surfaces including contours selected from the group consisting of bevels, chamfers, curves, and combinations thereof.

* * * * *